(12) United States Patent
Matsuda et al.

(10) Patent No.: US 8,512,709 B2
(45) Date of Patent: Aug. 20, 2013

(54) MODIFIED AMYLOID β PEPTIDE

(75) Inventors: Junichi Matsuda, Kikuchi (JP);
Kazuyoshi Kaminaka, Kikuchi (JP);
Chikateru Nozaki, Kikuchi (JP)

(73) Assignee: The Chemo-Sero-Therapeutic Research Institue, Kumamoto-shi (JP)

( * ) Notice: Subject to any disclaimer, the term of this patent is extended or adjusted under 35 U.S.C. 154(b) by 38 days.

(21) Appl. No.: 13/124,260

(22) PCT Filed: Oct. 16, 2009

(86) PCT No.: PCT/JP2009/067918
§ 371 (c)(1),
(2), (4) Date: Jul. 11, 2011

(87) PCT Pub. No.: WO2010/044464
PCT Pub. Date: Apr. 22, 2010

(65) Prior Publication Data
US 2011/0268756 A1 Nov. 3, 2011

(30) Foreign Application Priority Data
Oct. 16, 2008 (JP) .................. 2008-267992

(51) Int. Cl.
*A61K 38/17* (2006.01)
*A61K 39/00* (2006.01)
*A61P 25/00* (2006.01)
*A61P 37/04* (2006.01)
*C07K 14/435* (2006.01)

(52) U.S. Cl.
USPC ..... 424/185.1; 514/17.7; 514/17.8; 514/21.3; 514/21.4; 530/324; 530/325; 530/326

(58) Field of Classification Search
None
See application file for complete search history.

(56) References Cited

U.S. PATENT DOCUMENTS

| | | | |
|---|---|---|---|
| 5,589,154 A * | 12/1996 | Anderson | ........... 424/1.41 |
| 2003/0068325 A1 | 4/2003 | Wang | |
| 2006/0018918 A1 | 1/2006 | Chang | |
| 2007/0161088 A1 | 7/2007 | Arumugham et al. | |
| 2008/0145373 A1 | 6/2008 | Arumugham et al. | |
| 2008/0299074 A1 | 12/2008 | Arumugham et al. | |
| 2009/0311225 A1 | 12/2009 | Koduri | |
| 2010/0291122 A1 | 11/2010 | Matsuda et al. | |
| 2011/0287042 A1 | 11/2011 | Arumugham et al. | |

FOREIGN PATENT DOCUMENTS

| | | | |
|---|---|---|---|
| DE | 199 16417 | * | 4/1999 |
| JP | 2005 506311 | | 3/2005 |
| WO | WO 99/08695 | | 2/1999 |
| WO | WO/03/015812 | * | 2/2003 |
| WO | WO 2005/058941 A2 | | 6/2005 |
| WO | WO 2007/059190 A2 | | 5/2007 |
| WO | WO 2008/133208 A1 | | 11/2008 |

OTHER PUBLICATIONS

Tjernberg et al. 1996 "Arrest of β-amyloid fibril formation by a pentapeptide ligand" JBC 271(15):8545-8548.*
Vickers 2002 "A vaccine against alzheimer's disease: developments to date" drugs aging 19(7):487-494.*
The Extended European Search Report issued Feb. 24, 2012, in Application No. / Patent No. 09820642.8.
R. M. Kondratenko, et al., "Synthesis and immunostimulating activity of cysteine-containing derivatives of glycyrrhizic acid", Russian Journal of Bioorganic Chemistry, vol. 30, No. 1, XP009156430, Jan. 1, 2004, pp. 53-59.
Martha Savaria Morris, et al., "Homocysteine and Alzheimer's disease", The Lancet, Neurology, vol. 2, No. 7, (XP004810149), Jul. 1, 2003, pp. 425-428.
Takahashi, H., et al., "Monoclonal antibody to β peptide, recognizing amyloid deposits, neuronal cells and lipofuscin pigments in systemic organs," Acta Neuropathologica, vol. 85, No. 2, pp. 159-166, (1993).
Rzepczyk, C.M., et al., "Synthetic Peptide Immunogens Eliciting Antibodies to *Plasmodium falciparum* Sporozoite and Merozoite Surface Antigens in H-2[b] and H-2[k] Mice[1]," The Journal of Immunology, vol. 145, No. 8, pp. 2691-2696, (Oct. 15, 1990).
Gilman, S., et al., "Clinical effects of Aβ immunization (AN1792) in patients with AD in an interrupted trial," Neurology, vol. 64, pp. 1553-1562, (2005).
Agadjanyan, M.G., et al., "Prototype Alzheimer's Disease Vaccine Using the Immunodominant B Cell Epitope from β-Amyloid and Promiscuous T Cell Epitope Pan HLA DR-Binding Peptide[1]," The Journal of Immunology, vol. 174, pp. 1580-1586, (2005).
Bard, F., et al., "Epitope and isotype specificities of antibodies to β-amyloid peptide for protection against Alzheimer's disease-like neuropathology," Proc. Natl. Acad. Sci., vol. 100, No. 4, pp. 2023-2028, (Feb. 18, 2003).
Wang, C.Y., et al., "Site-specific UBITh® amyloid-β vaccine for immunotherapy of Alzheimer's disease," Vaccine, vol. 25, pp. 3041-3052, (Jan. 19, 2007).
International Search Report issued Nov. 17, 2009 in PCT/JP09/067918 filed Oct. 16, 2009.
U.S. Appl. No. 13/220,452, filed Aug. 29, 2011, Matsuda, et al.

* cited by examiner

*Primary Examiner* — Jeffrey Stucker
*Assistant Examiner* — Adam M Weidner
(74) *Attorney, Agent, or Firm* — Oblon, Spivak, McClelland, Maier & Neustadt, L.L.P.

(57) ABSTRACT

An object of the invention is to provide a peptide based on a sequence of an amyloid β peptide that may allow for induction of enhanced immune response and is safe and efficacious for prophylaxis and treatment of Alzheimer disease. An amyloid β peptide or a portion thereof with addition or insertion of cysteine or a cysteine analogue, and a method for enhancing immune response to amyloid β using said peptide, a medicament for prophylaxis and treatment of Alzheimer disease using said amyloid β peptide that induces an enhanced immune response, and a DNA vaccine comprising a gene coding for an amyloid β peptide or a sequence derived from an amyloid β peptide with addition or insertion of cysteine or a cysteine analogue, as expected to be similarly efficacious.

18 Claims, 1 Drawing Sheet

A peptide consisting of two 28-amino acid Aβ peptides with addition of one cysteine at the C-terminal bound to each other via a disulfide bond (28AACdisulfide28AAC):

N-terminal -DAEFRHDSGYEVHHQKLVFFAEDVGSNK-C
              ‖
N-terminal -DAEFRHDSGYEVHHQKLVFFAEDVGSNK-C A peptide consisting of two 28-amino acid Aβ peptides with addition of two cysteines at the C-terminal bound to each other via a disulfide bond (28AACCdisulfide28AACC):

N-terminal -DAEFRHDSGYEVHHQKLVFFAEDVGSNK-CC     With a disulfide bond formed
              ‖                                  between cysteines each at the N-terminal
N-terminal -DAEFRHDSGYEVHHQKLVFFAEDVGSNK-CC N-terminal -DAEFRHDSGYEVHHQKLVFFAEDVGSNK-CC     With a disulfide bond formed between
                                          ‖    cysteines each at the C-terminal
N-terminal -DAEFRHDSGYEVHHQKLVFFAEDVGSNK-CC N-terminal -DAEFRHDSGYEVHHQKLVFFAEDVGSNK-CC     With a disulfide bond formed between
                                  ‖            cysteine at the N-terminal and cysteine
N-terminal-DAEFRHDSGYEVHHQKLVFFAEDVGSNK-CC     at the C-terminal N-terminal -DAEFRHDSGYEVHHQKLVFFAEDVGSNK-CC     With disulfide bonds each formed between
              ‖‖‖‖                              cysteines each at the N-terminal and
N-terminal -DAEFRHDSGYEVHHQKLVFFAEDVGSNK-CC     between cysteines each at the C-terminal CC-KNSGVDEAFFVLKQHHVEYGSDHRFEAD-N-terminal
                            ‖‖‖‖
N-terminal -DAEFRHDSGYEVHHQKLVFFAEDVGSNK-CC     With disulfide bonds each formed between
                                                cysteine at the N-terminal and cysteine
                                                at the C-terminal A peptide consisting of 28-amino acid Aβ peptide with addition of one cysteine at the C-terminal and 28-amino acid Aβ peptide with addition of two cysteines at the C-terminal bound to each other via a disulfide bond (28AACdisulfide28AACC):

N-terminal -DAEFRHDSGYEVHHQKLVFFAEDVGSNK-CC
              ‖
N-terminal-DAEFRHDSGYEVHHQKLVFFAEDVGSNK-C N-terminal-DAEFRHDSGYEVHHQKLVFFAEDVGSNK-CC
                                  ‖
N-terminal-DAEFRHDSGYEVHHQKLVFFAEDVGSNK-C 28AACC(28AAC)-bound product consisting of plural 28-amino acid Aβ peptides with addition of two cysteines at the C-terminal bound to each other via disulfide bonds (28AACC(N)):

‖
N-terminal -DAEFRHDSGYEVHHQKLVFFAEDVGSNK-CC
                                          ‖
N-terminal-DAEFRHDSGYEVHHQKLVFFAEDVGSNK-CC
                                          ‖
N-terminal-DAEFRHDSGYEVHHQKLVFFAEDVGSNK-CC
                                          ‖
N-terminal-DAEFRHDSGYEVHHQKLVFFAEDVGSNK-CC
                                          ‖
N-terminal-DAEFRHDSGYEVHHQKLVFFAEDVGSNK-CC
                                          ‖

SEQUENCE LISTING

<160> NUMBER OF SEQ ID NOS: 53

<210> SEQ ID NO 1
<211> LENGTH: 42
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

```
Gly Leu Met Val Gly Gly Val Val Ile Ala
        35                  40

<210> SEQ ID NO 2
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asp Ala Glu Phe Arg His Asp Ser Gly Tyr Lys Gly Ala Ile Ile Gly
1               5                   10                  15

Leu Met Val Gly Gly Val Val Ile Ala Cys
            20                  25

<210> SEQ ID NO 3
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asp Ala Glu Phe Arg His Asp Ser Gly Tyr Lys Gly Ala Ile Ile Gly
1               5                   10                  15

Leu Met Val Gly Gly Val Val Ile Cys
            20                  25

<210> SEQ ID NO 4
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asp Ala Glu Phe Arg His Asp Ser Gly Tyr Lys Gly Ala Ile Ile Gly
1               5                   10                  15

Leu Met Val Gly Gly Val Val Cys
            20

<210> SEQ ID NO 5
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Ala Glu Phe Arg His Asp Ser Gly Tyr Lys Gly Ala Ile Ile Gly
1               5                   10                  15

Leu Met Val Gly Gly Val Cys
            20

<210> SEQ ID NO 6
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 6

Asp Ala Glu Phe Arg His Asp Ser Gly Tyr Lys Gly Ala Ile Ile Gly
1               5                  10                  15

Leu Met Val Gly Gly Cys
            20

<210> SEQ ID NO 7
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asp Ala Glu Phe Arg His Asp Ser Gly Tyr Lys Gly Ala Ile Ile Gly
1               5                  10                  15

Leu Met Val Gly Cys
            20

<210> SEQ ID NO 8
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asp Ala Glu Phe Arg His Asp Ser Gly Tyr Lys Gly Ala Ile Ile Gly
1               5                  10                  15

Leu Met Val Cys
            20

<210> SEQ ID NO 9
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asp Ala Glu Phe Arg His Asp Ser Gly Lys Gly Ala Ile Ile Gly Leu
1               5                  10                  15

Met Val Gly Cys
            20

<210> SEQ ID NO 10
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala Glu Phe Arg His Asp Ser Gly Tyr Lys Gly Ala Ile Ile Gly Leu
1               5                  10                  15

Met Val Gly Cys
            20

<210> SEQ ID NO 11
<211> LENGTH: 19
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Glu Phe Arg His Asp Ser Gly Tyr Lys Gly Ala Ile Ile Gly Leu Met
1               5                   10                  15

Val Gly Cys

<210> SEQ ID NO 12
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Glu Phe Arg His Asp Ser Gly Lys Gly Ala Ile Ile Gly Leu Met
1               5                   10                  15

Val Gly Cys

<210> SEQ ID NO 13
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Ala Glu Phe Arg His Asp Ser Gly Tyr Glu Val His His Gln Lys
1               5                   10                  15

Leu Val Lys Gly Ala Ile Ile Gly Leu Met Val Gly Gly Val Val Ile
                20                  25                  30

Ala Cys

<210> SEQ ID NO 14
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asp Ala Glu Phe Arg His Asp Ser Gly Tyr Glu Val His His Gln Lys
1               5                   10                  15

Leu Val Cys Phe Phe Ala Glu Asp Val Gly Ser Asn
                20                  25

<210> SEQ ID NO 15
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Ala Glu Phe Arg His Asp Ser Gly Tyr Glu Val His His Gln Lys
1               5                   10                  15

Leu Val Cys Phe Phe Ala Glu Asp Val Gly Ser
```

```
                    20                  25

<210> SEQ ID NO 16
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asp Ala Glu Phe Arg His Asp Ser Gly Tyr Glu Val His His Gln Lys
1               5                   10                  15

Leu Val Cys Phe Phe Ala Glu Asp Val Gly Ser Asn Lys Cys
            20                  25                  30

<210> SEQ ID NO 17
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asp Ala Glu Phe Arg His Asp Ser Gly Tyr Glu Val His His Gln Lys
1               5                   10                  15

Leu Val Cys Lys Gly Ala Ile Ile Gly Leu Met Val Gly
            20                  25

<210> SEQ ID NO 18
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Asp Ala Glu Phe Arg His Asp Ser Gly Tyr Glu Val His His Gln Lys
1               5                   10                  15

Leu Val Cys Lys Gly Ala Ile Ile Gly Leu Met Val Gly Cys
            20                  25                  30

<210> SEQ ID NO 19
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (29)..(29)
<223> OTHER INFORMATION: Homocysteine

<400> SEQUENCE: 19

Asp Ala Glu Phe Arg His Asp Ser Gly Tyr Glu Val His His Gln Lys
1               5                   10                  15

Leu Val Phe Phe Ala Glu Asp Val Gly Ser Asn Lys Xaa
            20                  25

<210> SEQ ID NO 20
<211> LENGTH: 29
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 20

Asp Ala Glu Phe Arg His Asp Ser Gly Tyr Glu Val His His Gln Lys
1               5                   10                  15

Leu Val Phe Phe Ala Glu Asp Val Gly Ser Asn Lys Cys
            20                  25

<210> SEQ ID NO 21
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Ala Glu Phe Arg His Asp Ser Gly Tyr Glu Val His His Gln Lys
1               5                   10                  15

Leu Val Phe Phe Ala Glu Asp Val Gly Ser Asn Lys Cys Cys
            20                  25                  30

<210> SEQ ID NO 22
<211> LENGTH: 126
<212> TYPE: DNA
<213> ORGANISM: Homo sapiens

<400> SEQUENCE: 22
gatgcagaat tccgacatga ctcaggatat gaagttcatc atcaaaaatt ggtgttcttt       60
gcagaagatg tgggttcaaa caaaggtgca atcattggac tcatggtggg cggtgttgtc      120
atagcg                                                                 126

<210> SEQ ID NO 23
<211> LENGTH: 78
<212> TYPE: DNA
<213> ORGANISM: Artificial Sequence
<220> FEATURE:
<223> OTHER INFORMATION: Description of Artificial Sequence: Synthetic
      coding oligonucleotide for amino acids of the
      synthetic peptides

<400> SEQUENCE: 23
gatgcagaat tccgacatga ctcaggatat aaaggtgcaa tcattggact catggtgggc       60
ggtgttgtca tagcgtgt                                                     78

<210> SEQ ID NO 24
<211> LENGTH: 75
<212> TYPE: DNA
<213> ORGANISM: Artificial Sequence
<220> FEATURE:
<223> OTHER INFORMATION: Description of Artificial Sequence: Synthetic
      coding oligonucleotide for amino acids of the
      synthetic peptides

<400> SEQUENCE: 24
gatgcagaat tccgacatga ctcaggatat aaaggtgcaa tcattggact catggtgggc       60
ggtgttgtca tatgt                                                        75

<210> SEQ ID NO 25
<211> LENGTH: 72
<212> TYPE: DNA
<213> ORGANISM: Artificial Sequence
<220> FEATURE:
```

<223> OTHER INFORMATION: Description of Artificial Sequence: Synthetic
      coding oligonucleotide for amino acids of the
      synthetic peptides

<400> SEQUENCE: 25
gatgcagaat tccgacatga ctcaggatat aaaggtgcaa tcattggact catggtgggc    60
ggtgttgtct gt    72

<210> SEQ ID NO 26
<211> LENGTH: 69
<212> TYPE: DNA
<213> ORGANISM: Artificial Sequence
<220> FEATURE:
<223> OTHER INFORMATION: Description of Artificial Sequence: Synthetic
      coding oligonucleotide for amino acids of the
      synthetic peptides

<400> SEQUENCE: 26
gatgcagaat tccgacatga ctcaggatat aaaggtgcaa tcattggact catggtgggc    60
ggtgtttgt    69

<210> SEQ ID NO 27
<211> LENGTH: 66
<212> TYPE: DNA
<213> ORGANISM: Artificial Sequence
<220> FEATURE:
<223> OTHER INFORMATION: Description of Artificial Sequence: Synthetic
      coding oligonucleotide for amino acids of the
      synthetic peptides

<400> SEQUENCE: 27
gatgcagaat tccgacatga ctcaggatat aaaggtgcaa tcattggact catggtgggc    60
ggttgt    66

<210> SEQ ID NO 28
<211> LENGTH: 63
<212> TYPE: DNA
<213> ORGANISM: Artificial Sequence
<220> FEATURE:
<223> OTHER INFORMATION: Description of Artificial Sequence: Synthetic
      coding oligonucleotide for amino acids of the
      synthetic peptides

<400> SEQUENCE: 28
gatgcagaat tccgacatga ctcaggatat aaaggtgcaa tcattggact catggtgggc    60
tgt    63

<210> SEQ ID NO 29
<211> LENGTH: 60
<212> TYPE: DNA
<213> ORGANISM: Artificial Sequence
<220> FEATURE:
<223> OTHER INFORMATION: Description of Artificial Sequence: Synthetic
      coding oligonucleotide for amino acids of the
      synthetic peptides

<400> SEQUENCE: 29
gatgcagaat tccgacatga ctcaggatat aaaggtgcaa tcattggact catggtgtgt    60

<210> SEQ ID NO 30
<211> LENGTH: 60
<212> TYPE: DNA
<213> ORGANISM: Artificial Sequence
<220> FEATURE:
<223> OTHER INFORMATION: Description of Artificial Sequence: Synthetic
      coding oligonucleotide for amino acids of the synthetic peptides

<400> SEQUENCE: 30
gatgcagaat tccgacatga ctcaggaaaa ggtgcaatca ttggactcat ggtgggctgt     60

<210> SEQ ID NO 31
<211> LENGTH: 60
<212> TYPE: DNA
<213> ORGANISM: Artificial Sequence
<220> FEATURE:
<223> OTHER INFORMATION: Description of Artificial Sequence: Synthetic
      coding oligonucleotide for amino acids of the
      synthetic peptides

<400> SEQUENCE: 31
gcagaattcc gacatgactc aggatataaa ggtgcaatca ttggactcat ggtgggctgt     60

<210> SEQ ID NO 32
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gaattccgac atgactcagg atataaaggt gcaatcattg actcatggt gggctgt          57

<210> SEQ ID NO 33
<211> LENGTH: 57
<212> TYPE: DNA
<213> ORGANISM: Artificial Sequence
<220> FEATURE:
<223> OTHER INFORMATION: Description of Artificial Sequence: Synthetic
      coding oligonucleotide for amino acids of the
      synthetic peptides

<400> SEQUENCE: 33
gcagaattcc gacatgactc aggaaaaggt gcaatcattg actcatggt gggctgt          57

<210> SEQ ID NO 34
<211> LENGTH: 102
<212> TYPE: DNA
<213> ORGANISM: Artificial Sequence
<220> FEATURE:
<223> OTHER INFORMATION: Description of Artificial Sequence: Synthetic
      coding polynucleotide for amino acids of the
      synthetic peptides

<400> SEQUENCE: 34
gatgcagaat tccgacatga ctcaggatat gaagttcatc atcaaaaatt ggtgaaaggt     60
gcaatcattg gactcatggt gggcggtgtt gtcatagcgt gt                       102

<210> SEQ ID NO 35
<211> LENGTH: 84
<212> TYPE: DNA
<213> ORGANISM: Artificial Sequence
<220> FEATURE:
<223> OTHER INFORMATION: Description of Artificial Sequence: Synthetic
      coding oligonucleotide for amino acids of the
      synthetic peptides

<400> SEQUENCE: 35
gatgcagaat tccgacatga ctcaggatat gaagttcatc atcaaaaatt ggtgtgtttc     60
tttgcagaag atgtgggttc aaac                                            84

```
<210> SEQ ID NO 36
<211> LENGTH: 81
<212> TYPE: DNA
<213> ORGANISM: Artificial Sequence
<220> FEATURE:
<223> OTHER INFORMATION: Description of Artificial Sequence: Synthetic
      coding oligonucleotide for amino acids of the
      synthetic peptides

<400> SEQUENCE: 36
gatgcagaat tccgacatga ctcaggatat gaagttcatc atcaaaaatt ggtgtgtttc      60
tttgcagaag atgtgggttc a                                                81

<210> SEQ ID NO 37
<211> LENGTH: 90
<212> TYPE: DNA
<213> ORGANISM: Artificial Sequence
<220> FEATURE:
<223> OTHER INFORMATION: Description of Artificial Sequence: Synthetic
      coding oligonucleotide for amino acids of the
      synthetic peptides

<400> SEQUENCE: 37
gatgcagaat tccgacatga ctcaggatat gaagttcatc atcaaaaatt ggtgtgtttc      60
tttgcagaag atgtgggttc aaacaaatgt                                       90

<210> SEQ ID NO 38
<211> LENGTH: 87
<212> TYPE: DNA
<213> ORGANISM: Artificial Sequence
<220> FEATURE:
<223> OTHER INFORMATION: Description of Artificial Sequence: Synthetic
      coding oligonucleotide for amino acids of the
      synthetic peptides

<400> SEQUENCE: 38
gatgcagaat tccgacatga ctcaggatat gaagttcatc atcaaaaatt ggtgtgtaaa      60
ggtgcaatca ttggactcat ggtgggc                                          87

<210> SEQ ID NO 39
<211> LENGTH: 90
<212> TYPE: DNA
<213> ORGANISM: Artificial Sequence
<220> FEATURE:
<223> OTHER INFORMATION: Description of Artificial Sequence: Synthetic
      coding oligonucleotide for amino acids of the
      synthetic peptides

<400> SEQUENCE: 39
gatgcagaat tccgacatga ctcaggatat gaagttcatc atcaaaaatt ggtgtgtaaa      60
ggtgcaatca ttggactcat ggtgggctgt                                       90

<210> SEQ ID NO 40
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Asp Ala Glu Phe Arg His Asp Ser Gly Tyr Ala Ile Ile Gly Leu Met
1               5                   10                  15

Val Gly Gly Val Val Ile Ala Cys
            20
```

<210> SEQ ID NO 41
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Asp Ala Glu Phe Arg His Asp Ser Gly Tyr Gly Ala Ile Ile Gly Leu
1               5                   10                  15

Met Val Gly Gly Val Val Ile Ala Cys
            20                  25

<210> SEQ ID NO 42
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Asp Ala Glu Phe Arg His Asp Ser Gly Tyr Lys Gly Ala Ile Ile Gly
1               5                   10                  15

Leu Met Val Gly Gly Val Val Ile Ala
            20                  25

<210> SEQ ID NO 43
<211> LENGTH: 40
<212> TYPE: PRT
<213> ORGANISM: Homo sapiens

<400> SEQUENCE: 43

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 44
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Asp Ala Glu Phe Arg His Asp Ser Gly Tyr Lys Gly Ala Ile Ile Gly
1               5                   10                  15

Leu Met Cys

<210> SEQ ID NO 45
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Asp Ala Glu Phe Arg His Asp Ser Gly Tyr Lys Gly Ala Ile Ile Gly
1               5                   10                  15

Leu Cys

<210> SEQ ID NO 46
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Asp Ala Glu Phe Arg His Asp Ser Lys Gly Ala Ile Ile Gly Leu Met
1               5                   10                  15

Val Gly Cys

<210> SEQ ID NO 47
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Asp Ala Glu Phe Arg His Asp Lys Gly Ala Ile Ile Gly Leu Met Val
1               5                   10                  15

Gly Cys

<210> SEQ ID NO 48
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Phe Arg His Asp Ser Gly Tyr Lys Gly Ala Ile Ile Gly Leu Met Val
1               5                   10                  15

Gly Cys

<210> SEQ ID NO 49
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Asp Ala Glu Phe Arg His Asp Ser Gly Tyr Glu Val His His Gln Lys
1               5                   10                  15

Leu Val Cys Phe Phe Ala Glu Asp Val Gly Ser Asn Lys
                20                  25

<210> SEQ ID NO 50
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Asp Ala Glu Phe Arg His Asp Ser Gly Tyr Glu Val His His Gln Lys

-continued

```
                1               5                  10              15
Leu Val Cys Phe Phe Ala Glu Asp Val Gly
                20                  25

<210> SEQ ID NO 51
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Asp Ala Glu Phe Arg His Asp Ser Gly Tyr Glu Val His His Gln Lys
1               5                  10                  15

Leu Val Lys Gly Ala Ile Ile Gly Leu Met Val Gly Cys
                20                  25

<210> SEQ ID NO 52
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Asp Ala Glu Phe Arg His Asp Ser Gly Tyr Glu Val His His Gln Lys
1               5                  10                  15

Leu Val Lys Gly Ala Ile Ile Gly Leu Met Val Gly
                20                  25

<210> SEQ ID NO 53
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (29)..(29)
<223> OTHER INFORMATION: Glutathione

<400> SEQUENCE: 53

Asp Ala Glu Phe Arg His Asp Ser Gly Tyr Glu Val His His Gln Lys
1               5                  10                  15

Leu Val Phe Phe Ala Glu Asp Val Gly Ser Asn Lys Xaa
                20                  25
```

MODIFIED AMYLOID β PEPTIDE

TECHNICAL FIELD

The present invention relates to a method for enhancing an immune response-inducing ability of an amyloid β (hereinafter referred to as "Aβ") peptide. More specifically, the present invention relates to a medicament for prophylaxis and treatment of Alzheimer disease comprising a peptide derived from Aβ, the causative agent of Alzheimer disease, or a portion thereof, in which cysteine or its analogue is added or inserted.

BACKGROUND ART

Alzheimer disease is one of dementia and is associated with declined cognitive function and change in personality as principal symptoms. With the progress of aging population, the number of Alzheimer disease patients keeps increasing. It is expected that the number of patients in Japan, the United States and Europe will become 7.3 million in 2014 from 5.6 million in 2004. Therefore, early development of a medicament for prophylaxis and treatment of Alzheimer disease is earnestly desired.

Alzheimer disease's pathological indications include three features of atrophy and/or fall-off of neurons, formation of senile plaques due to aggregation and/or deposition of Aβ and neurofibrillary changes due to abnormal tau proteins. Alzheimer disease is classified into major two groups, i.e. familial Alzheimer disease and solitary Alzheimer disease. For the former, causative genetic mutation has been identified and its phenotype was found to elucidate that increase in production of amyloid β peptide, especially Aβ1-42 consisting of 42 amino acid residues, in the brain is a major cause of the disease. However, a ratio of patients diagnosed to suffer from familial Alzheimer disease in a strict sense is 1% or less among the total patients. It is for solitary Alzheimer disease that accounts for 99% of patients that the most prompt elucidation of cause of the disease is desired. It is thought that solitary Alzheimer disease is caused by duplication of unidentified genetic risk factors, the presence of recessive gene, the presence of environmental risk factors, and the like. At present, based on the fact that genetic mutations in familial Alzheimer disease are common in ultimate increase in highly aggregating Aβ42, it is thought that the major cause of solitary Alzheimer disease, as undergoing similar pathological development to that of familial Alzheimer disease, may be increase in Aβ42. This idea is called a hypothesis of myeloid and at present investigation for the treatment is under progress based on this hypothesis.

Aβ is produced from its precursor protein via cleavage with a membrane-bound aspartate protease. β-Secretase cleaves the N-terminal of Aβ whereas γ-secretases cleaves the C-terminal thereof. A cleaved Aβ may after a while secreted out of the cells depending upon the synaptic activity. Aβ rapidly auto-aggregates so that a monomer Aβ, via a dimer, trimer and a soluble oligomer, forms protofibril, a prefibrous structure, which then forms and accumulates insoluble amyloid fiber. It has now become a major idea that negative effects of aggregated soluble Aβ oligomer to the nerve play an important role in pathological conditions of Alzheimer disease. A number of forms of soluble Aβ oligomer that may block neurotransmission have been reported, including a dimer, a trimer, an amylospheroid (53 kDa aggregate), Aβ56 (56 kDa aggregate), aggregates of up to 40 amino acid length, and the like.

At present, approach for therapy through clearance of Aβ, which may play a highly important role in mechanism for onset of Alzheimer disease, is widely done, among which is a study of an antibody therapy with an antibody to Aβ. It is thought that action mechanism of Aβ clearance by an anti-Aβ antibody includes phagocytosis by microglia via Fc receptor of an antibody, accelerated dissolution or suppressed aggregation of fibrous Aβ and binding of the antibody to Aβ in blood to accelerate exclusion of soluble Aβ form the brain. Two approaches are proposed, i.e. active immunity where an anti-Aβ antibody is induced by a vaccine and passive immunity where an anti-Aβ antibody per se is administered.

For the former approach, vaccine AN1792 with the use of Aβ per se as an antigen proceeded to phase II clinical test but the test discontinued since 6% patients suffered from cerebrospinal meningitis during the test. However, difference in part of high-order function was observed between patients who had an increased antibody titer and patients who had not (Non-patent reference 1). Besides, the brain of patient died during the clinical test was examined to reveal that senile plaque disappeared in the neocortex. Moreover, MRI before and after administration showed that the administration group exhibited a less volume of the brain than that of the placebo group. As such, although the clinical test discontinued due to adverse side effects, it was also proved that a vaccine with the use of Aβ per se as an antigen was efficacious. In future, development of a safer vaccine is desired.

It is thought that cerebrospinal meningitis is caused by AN1792 as a consequence of the use of a potent adjuvant QS21 and cellular immunity induced by a T cell epitope present in Aβ sequence per se. Plenty of investigation has been done for a T cell epitope present in Aβ sequence per se to reveal that, at least in the N-terminal of Aβ sequence of residues 1-10, a T cell epitope that may induce humoral immunity is present but a T cell epitope that may induce cellular immunity is not present (Patent references 2-4).

Non-patent reference 1: Gilman S, Koller M, Black R S, Jenkins L, et al., NEUROLOGY, 2005; 64: p 1553-1562
Non-patent reference 2: Michael G, Agadjanyan M G, et al., Journal of Immunology, 2005; 174: p 1580-1586
Non-patent reference 3: Bard F, Barbour R, Cannon C, Carretto R, Fox M, et al., Proc. Natl. Acad. Sci. USA, 2003; 100: p 2023-2028
Non-patent reference 4: Wanga C Y. et al., Vaccine, 2007; 25: p 3041-3052

DISCLOSURE OF THE INVENTION

Technical Problem to be Solved by the Invention

As described above, there is a concern for adverse side effects in a vaccine therapy for Alzheimer disease with a combination of a full length of Aβ sequence with a potent adjuvant such as QS21. Thus, development of a safer and more efficacious method for prophylaxis and treatment with a combination of an Aβ peptide in a safer form with a safer adjuvant is desired. Accordingly, an object of the present invention is to provide a peptide for a safer vaccine therapy of Alzheimer disease by devising the form of an Aβ peptide.

Means for Solving the Problems

The present inventors have earnestly investigated a method for immunization and for enhancing immunization that is safe for the living body, efficacious and inexpensive, and as a result, have found that a capacity of inducing an enhanced immune response of a peptide of interest may be enhanced by addition or insertion of a cysteine residue, an amino acid constituting a naturally-occurring protein, to thereby show that property of inducing an enhanced immune response against Aβ may be obtained by adding or inserting a cysteine molecule to a portion of Aβ peptide without using a full length of Aβ peptide (PCT/JP2008/057612). In accordance with the present invention, further investigation resulted in finding of a method for an obtaining enhanced immune response to Aβ and novel Aβ peptides with addition of a cysteine molecule that are expected to induce a reduced cellular immune response.

The present invention relates to a novel method for enhancing an immune response, more specifically, a method for enhancing an immune response characterized by that a cysteine molecule is added or inserted to an immunogenic peptide and encompasses the inventions as follows:

(1) A peptide characterized by that cysteine or a cysteine analogue is added to or inserted into a portion of an amyloid β peptide or a sequence derived from an amyloid β peptide, said peptide being selected from (A) to (F) as follows:

(A) a peptide consisting of (a) a peptide consisting of the amino acid residues No. 1 to No. 18 from the N-terminal of SEQ ID NO:1 or a peptide consisting of a portion of the amino acid residues No. 1 to No. 18 from the N-terminal of SEQ ID NO:1 and (b) a peptide consisting of 9 or more amino acid residues including the amino acid residues No. 28 to No. 36 from the N-terminal of SEQ ID NO:1 within the amino acid residues No. 28 to No. 42 from the N-terminal of SEQ ID NO:1, the peptide (a) and the peptide (b) being bound to each other, wherein cysteine or a cysteine analogue is bound to the C-terminal of the resulting combination of the peptide (a) and the peptide (b);

(B) a peptide consisting of the amino acid residues No. 1 to 26 or No. 1 to No. 27 from the N-terminal of SEQ ID NO:1 wherein cysteine or a cysteine analogue is inserted between the amino acid residues Nos. 18 and 19 from the N-terminal;

(C) a peptide consisting of the amino acid sequence of SEQ ID NO:1 or a peptide consisting of a portion of the amino acid sequence of SEQ ID NO:1, wherein cysteine or a cysteine analogue is inserted between the amino acid residues Nos. 18 and 19 from the N-terminal, and wherein cysteine or a cysteine analogue is bound to the C-terminal of said peptide;

(D) a peptide consisting of the amino acid residues No. 1 to No. 18 from the N-terminal of SEQ ID NO:1 or a peptide consisting of a portion of the amino acid residues No. 1 to No. 18 from the N-terminal of SEQ ID NO:1, to the C-terminal of which cysteine or a cysteine analogue is bound, to which a peptide consisting of the amino acid residues No. 28 to No. 42 from the N-terminal of SEQ ID NO:1 or a peptide consisting of a portion of the amino acid residues No. 28 to No. 42 from the N-terminal of SEQ ID NO:1 is further bound, to the C-terminal of which cysteine or a cysteine analogue is optionally bound;

(E) a peptide consisting of the amino acid sequence of SEQ ID NO:1 or a peptide consisting of a portion of the amino acid sequence of SEQ ID NO:1, to the C-terminal of which a cysteine analogue is bound;

(F) a peptide consisting of two or more of a peptide consisting of the amino acid sequence of SEQ ID NO:1 or a peptide consisting of a portion of the amino acid sequence of SEQ ID NO:1, to the C-terminal of which cysteine or a cysteine analogue is bound, said two or more of the peptides being bound to each other via a disulfide bond between said cysteines or said cysteine analogues.

(2) The peptide of (1) as above wherein the peptide of (A)(a) as above is selected from peptides consisting of the amino acid residues No. 1 to No. 10, No. 2 to No. 10, No. 3 to No. 10, No. 1 to No. 9, No. 2 to No. 9, No. 1 to No. 18 from the N-terminal of SEQ ID NO:1, and the peptide of (A)(b) as above is selected from peptides consisting of the amino acid residues No. 28 to No. 36, No. 28 to No. 37, No. 28 to No. 38, No. 28 to No. 39, No. 28 to No. 40, No. 28 to No. 41, No. 28 to No. 42 from the N-terminal of SEQ ID NO:1.

(3) The peptide of (1) as above wherein the peptide of (C) as above is a peptide consisting of the amino acid residues No. 1 to No. 28 from the N-terminal of SEQ ID NO:1, wherein cysteine or a cysteine analogue is inserted between the amino acid residues Nos. 18 and 19 from the N-terminal, and wherein cysteine or a cysteine analogue is bound to the C-terminal of said peptide.

(4) The peptide of (1) as above wherein the peptide of (D) as above is a peptide consisting of the amino acid residues No. 1 to No. 18 from the N-terminal of SEQ ID NO:1, to the C-terminal of which cysteine or a cysteine analogue is bound, to which a peptide consisting of the amino acid residues No. 28 to No. 37 from the N-terminal of SEQ ID NO:1 is further bound, to the C-terminal of which cysteine or a cysteine analogue is optionally bound.

(5) The peptide of (1) as above wherein the peptide of (E) as above is a peptide consisting of the amino acid residues No. 1 to No. 28 from the N-terminal of SEQ ID NO:1, to the C-terminal of which a cysteine analogue is bound.

(6) The peptide of (1) as above wherein the peptide of (F) as above is a peptide consisting of two or more of a peptide consisting of the amino acid residues No. 1 to No. 28 from the N-terminal of SEQ ID NO:1, to the C-terminal of which cysteine or a cysteine analogue is bound, wherein said two or more of the peptides are bound to each other via a disulfide bond between said cysteines or said cysteine analogues.

(7) The peptide of any one of (1) to (6) as above wherein said cysteine analogue is homocysteine.

(8) The peptide of any one of (1) to (7) as above wherein said peptide is a peptide selected from the group consisting of the following:

a peptide of any one of SEQ ID NO:2 to SEQ ID NO:19;

a peptide consisting of two peptides, each of which peptides consist of SEQ ID NO:20 and are bound to each other via a disulfide bond;

a peptide consisting of a peptide consisting of SEQ ID NO:20 and a peptide consisting of SEQ ID NO:21, each of which peptides are bound to each other via a disulfide bond;

a peptide consisting of two peptides, each of which peptide consist of SEQ ID NO:21 and are bound to each other via a disulfide bond; and a peptide consisting of plural peptides, each of which peptide consist of SEQ ID NO:21 and are bound to each other via a disulfide bond.

(9) A method for enhancing immune response to amyloid β characterized by that the peptide of any one of (1) to (8) as above is used.

(10) A medicament for prophylaxis and treatment of Alzheimer disease characterized by that the medicament comprises as an active ingredient the peptide of any one of (1) to (8) as above.

(11) A DNA vaccine effective for prophylaxis and treatment of Alzheimer disease characterized by that the vaccine comprises a gene fragment coding for the amino acid sequence of the peptide of any one of (1) to (8) as above.

The present invention also relates to a method for prophylaxis and treatment of Alzheimer disease in a mammal which comprises administering a pharmaceutically effective amount of the peptide of the present invention to said mammal as well as a method for prophylaxis and treatment of Alzheimer disease in a mammal which comprises administering a pharmaceutically effective amount of a gene fragment coding for the amino acid sequence of the peptide of the present invention to said mammal.

The present invention further relates to the use of the peptide of the present invention for the manufacture of a medicament for prophylaxis and treatment of Alzheimer disease as well as the use of the gene fragment coding for the amino acid sequence of the peptide of the present invention for the manufacture of a medicament for prophylaxis and treatment of Alzheimer disease.

Effects of the Invention

The present invention provides an immunogenic peptide that induces an enhanced and sufficient immune response to an Aβ peptide even if it is used alone without an adjuvant. According to the present invention, merely by addition or insertion of a cysteine molecule to a portion of an Aβ peptide or a sequence derived from an Aβ peptide, antibody production of an immunogenic peptide may be enhanced. Therefore, there is no disadvantage associated with the use of an adjuvant to allow for easier design of a drug formulation.

The immunogenic peptide of the present invention that induces an enhanced immune response to an Aβ peptide, when administered to the living body, may rapidly and abundantly induce an antibody specific to the peptide in blood. No toxicity of cysteine is known but rather cysteine and its related substances are known to have an antitoxic effect in the living body and therefore the immunogenic peptide of the present invention that induces an enhanced immune response may be used in the body very safely.

The immunogenic peptide of the present invention that induces an enhanced immune response may be prepared by a non-biological procedure by chemical synthesis without biological synthesis and hence in higher uniformity than the conventional component vaccines. Additionally, with the lowest risk of toxicity, infection and decrease in quality due to contamination, a safer vaccine may be provided.

A peptide preparation comprising the immunogenic peptide of the present invention that induces an enhanced immune response to an Aβ peptide may be administered not only by injection such as subcutaneous or intramuscular administration but also by oral, transnasal or transdermal administration, which would avoid stress and medical accidents caused by syringe needle.

BRIEF DESCRIPTION OF DRAWINGS

FIG. 1 shows a structure of Aβ peptides of 28 amino acid residues with addition of cysteine bound to each other via a disulfide bond. FIG. 1 discloses SEQ ID NOS: 20, 20, 21, 21, 21, 21, 21, 21, 21, 21, 21, 21, 20, 21, 20, 21, 21, 21, 21 and 21, respectively, in order of appearance.

BEST MODE FOR CARRYING OUT THE INVENTION

In accordance with the present invention, a cysteine molecule or a derivative thereof may directly be added or inserted to the peptide or alternatively a sequence expressing cysteine may be added or inserted to the DNA or RNA sequence. The position of addition and insertion of cysteine is not especially limited insofar as the immune response enhancing effect to an Aβ peptide may be obtained. The number of a cysteine molecule to be inserted may be one or more. When plural cysteine molecules are inserted, they may be inserted either consecutively or not consecutively. The simplest structure would be a portion of an Aβ peptide, to either the N-terminal or the C-terminal of which one cysteine is bound.

The peptide of the present invention effective for prophylaxis and treatment of Alzheimer disease may include a peptide that is a portion of, or is derived from, Aβ peptide (DAEFRHDSGYEVHHQKLVFFAEDVGSNKGAIIGLMVGGVVIA: SEQ ID NO:1) consisting of the amino acid residues No. 1 to No. 42, to which cysteine (Cys) or its analogue is added. Examples of such peptides include those listed hereinbelow. A cysteine analogue as used herein refers to a precursor and a metabolite of cysteine and includes typically homocysteine.

(A) A peptide comprising (a) a peptide consisting of the amino acid residues No. 1 to No. 18 from the N-terminal of SEQ ID NO:1 or a peptide consisting of a portion of the amino acid residues No. 1 to No. 18 from the N-terminal of SEQ ID NO:1 and (b) a peptide consisting of 9 or more amino acid residues including the amino acid residues No. 28 to No. 36 from the N-terminal of SEQ ID NO:1 within the amino acid residues No. 28 to No. 42 from the N-terminal of SEQ ID NO:1, the peptide (a) and the peptide (b) being bound to each other, wherein cysteine or a cysteine analogue is bound to the C-terminal of the resulting combination of the peptide (a) and the peptide (b)

(1) A peptide consisting of the amino acid residues No. 1 to No. 10 from the N-terminal of SEQ ID NO:1, to the C-terminal of which a peptide consisting of the amino acid residues No. 28 to No. 42 from the N-terminal of SEQ ID NO:1 is bound, to the C-terminal of which cysteine is added (1-10-28-42AACys):

(SEQ ID NO: 2)
N-terminal-DAEFRHDSGYKGAIIGLMVGGVVIAC (2) A peptide consisting of the amino acid residues No. 1 to No. 10 from the N-terminal of SEQ ID NO:1, to the C-terminal of which a peptide consisting of the amino acid residues No. 28 to No. 41 from the N-terminal of SEQ ID NO:1 is bound, to the C-terminal of which cysteine is added (1-10-28-41AACys):

(SEQ ID NO: 3)
N-terminal-DAEFRHDSGYKGAIIGLMVGGVVIC (3) A peptide consisting of the amino acid residues No. 1 to No. 10 from the N-terminal of SEQ ID NO:1, to the C-terminal of which a peptide consisting of the amino acid residues No. 28 to No. 40 from the N-terminal of SEQ ID NO:1 is bound, to the C-terminal of which cysteine is added (1-10-28-40AACys):

(SEQ ID NO: 4)
N-terminal-DAEFRHDSGYKGAIIGLMVGGVC (4) A peptide consisting of the amino acid residues No. 1 to No. 10 from the N-terminal of SEQ ID NO:1, to the C-terminal of which a peptide consisting of the amino acid residues No. 28 to No. 39 from the N-terminal of SEQ ID NO:1 is bound, to the C-terminal of which cysteine is added (1-10·28-39AACys):

```
                                             (SEQ ID NO: 5)
       N-terminal-DAEFRHDSGYKGAIIGLMVGGVC
```

(5) A peptide consisting of the amino acid residues No. 1 to No. 10 from the N-terminal of SEQ ID NO:1, to the C-terminal of which a peptide consisting of the amino acid residues No. 28 to No. 38 from the N-terminal of SEQ ID NO:1 is bound, to the C-terminal of which cysteine is added (1-10·28-38AACys):

```
                                             (SEQ ID NO: 6)
       N-terminal-DAEFRHDSGYKGAIIGLMVGGC
```

(6) A peptide consisting of the amino acid residues No. 1 to No. 10 from the N-terminal of SEQ ID NO:1, to the C-terminal of which a peptide consisting of the amino acid residues No. 28 to No. 37 from the N-terminal of SEQ ID NO:1 is bound, to the C-terminal of which cysteine is added (1-10·28-37AACys):

```
                                             (SEQ ID NO: 7)
       N-terminal-DAEFRHDSGYKGAIIGLMVGC
```

(7) A peptide consisting of the amino acid residues No. 1 to No. 10 from the N-terminal of SEQ ID NO:1, to the C-terminal of which a peptide consisting of the amino acid residues No. 28 to No. 36 from the N-terminal of SEQ ID NO:1 is bound, to the C-terminal of which cysteine is added (1-10·28-36AACys):

```
                                             (SEQ ID NO: 8)
       N-terminal-DAEFRHDSGYKGAIIGLMVC
```

(8) A peptide consisting of the amino acid residues No. 1 to No. 9 from the N-terminal of SEQ ID NO:1, to the C-terminal of which a peptide consisting of the amino acid residues No. 28 to No. 37 from the N-terminal of SEQ ID NO:1 is bound, to the C-terminal of which cysteine is added (1-9·28-37AACys):

```
                                             (SEQ ID NO: 9)
       N-terminal-DAEFRHDSGKGAIIGLMVGC
```

(9) A peptide consisting of the amino acid residues No. 2 to No. 10 from the N-terminal of SEQ ID NO:1, to the C-terminal of which a peptide consisting of the amino acid residues No. 28 to No. 37 from the N-terminal of SEQ ID NO:1 is bound, to the C-terminal of which cysteine is added (2-10·28-37AACys):

```
                                             (SEQ ID NO: 10)
       N-terminal-AEFRHDSGYKGAIIGLMVGC
```

(10) A peptide consisting of the amino acid residues No. 3 to No. 10 from the N-terminal of SEQ ID NO:1, to the C-terminal of which a peptide consisting of the amino acid residues No. 28 to No. 37 from the N-terminal of SEQ ID NO:1 is bound, to the C-terminal of which cysteine is added (3-10·28-37AACys):

```
                                             (SEQ ID NO: 11)
       N-terminal-EFRHDSGYKGAIIGLMVGC
```

(11) A peptide consisting of the amino acid residues No. 2 to No. 9 from the N-terminal of SEQ ID NO:1, to the C-terminal of which a peptide consisting of the amino acid residues No. 28 to No. 37 from the N-terminal of SEQ ID NO:1 is bound, to the C-terminal of which cysteine is added (2-9·28-37AACys):

```
                                             (SEQ ID NO: 12)
       N-terminal-AEFRHDSGKGAIIGLMVGC
```

(12) A peptide consisting of the amino acid residues No. 1 to No. 18 from the N-terminal of SEQ ID NO:1, to the C-terminal of which a peptide consisting of the amino acid residues No. 28 to No. 42 from the N-terminal of SEQ ID NO:1 is bound, to the C-terminal of which cysteine is added (1-18·28-42AACys):

```
                                             (SEQ ID NO: 13)
     N-terminal-DAEFRHDSGYEVHHQKLVKGAIIGLMVGGVVIAC
```

(B) A peptide consisting of the amino acid residues No. 1 to No. 26 or No. 1 to No. 27 from the N-terminal of SEQ ID NO:1 wherein cysteine or a cysteine analogue is inserted between the amino acid residues Nos. 18 and 19 from the N-terminal (1) A peptide consisting of the amino acid residues No. 1 to No. 27 from the N-terminal of SEQ ID NO:1 (hereinafter referred to as "27-amino acid Aβ peptide") wherein cysteine is inserted between the amino acid residues Nos. 18 and 19 from the N-terminal (1-18Cys19-27AA):

```
                                             (SEQ ID NO: 14)
       N-terminal-DAEFRHDSGYEVHHQKLVCFFAEDVGSN
```

(2) A peptide consisting of the amino acid residues No. 1 to No. 26 from the N-terminal of SEQ ID NO:1 (hereinafter referred to as "26-amino acid Aβ peptide") wherein cysteine is inserted between the amino acid residues Nos. 18 and 19 from the N-terminal (1-18Cys19-26AA):

```
                                             (SEQ ID NO: 15)
       N-terminal-DAEFRHDSGYEVHHQKLVCFFAEDVGS
```

(C) A peptide consisting of the amino acid sequence of SEQ ID NO:1 or a peptide consisting of a portion of the amino acid sequence of SEQ ID NO:1, wherein cysteine or a cysteine analogue is inserted between the amino acid residues Nos. 18 and 19 from the N-terminal, and wherein cysteine or a cysteine analogue is bound to the C-terminal of said peptide (1) A peptide consisting of the amino acid residues No. 1 to No. 28 from the N-terminal of SEQ ID NO:1 (hereinafter referred to as "28-amino acid Aβ peptide"), wherein cysteine is inserted between the amino acid residues Nos. 18 and 19 from the N-terminal, and wherein cysteine is bound to the C-terminal of said peptide (1-18Cys19-28AACys)

(SEQ ID NO: 16)
N-terminal-DAEFRHDSGYEVHHQKLV<u>C</u>FFAEDVGSNK<u>C</u>

(D) A peptide consisting of the amino acid residues No. 1 to No. 18 from the N-terminal of SEQ ID NO:1 or a peptide consisting of a portion of the amino acid residues No. 1 to No. 18 from the N-terminal of SEQ ID NO:1, to the C-terminal of which cysteine or a cysteine analogue is bound, to which a peptide consisting of the amino acid residues No. 28 to No. 42 from the N-terminal of SEQ ID NO:1 or a peptide consisting of a portion of the amino acid residues No. 28 to No. 42 from the N-terminal of SEQ ID NO:1 is further bound, to the C-terminal of which cysteine or a cysteine analogue is optionally bound (1) A peptide consisting of the amino acid residues No. 1 to No. 18 from the N-terminal of SEQ ID NO:1, to the C-terminal of which cysteine is bound, to which a peptide consisting of the amino acid residues No. 28 to No. 37 from the N-terminal of SEQ ID NO:1 is further bound (1-18Cys28-37AA)

(SEQ ID NO: 17)
N-terminal-DAEFRHDSGYEVHHQKLV<u>C</u>KGAIIGLMVG (2) A peptide consisting of the amino acid residues No. 1 to No. 18 from the N-terminal of SEQ ID NO:1, to the C-terminal of which cysteine is bound, to which a peptide consisting of the amino acid residues No. 28 to No. 37 from the N-terminal of SEQ ID NO:1 is further bound, to the C-terminal of which cysteine is bound (1-18Cys28-37AACys)

(SEQ ID NO: 18)
N-terminal-DAEFRHDSGYEVHHQKLV<u>C</u>KGAIIGLMVG<u>C</u>

(E) A peptide consisting of the amino acid sequence of SEQ ID NO:1 or a peptide consisting of a portion of the amino acid sequence of SEQ ID NO:1, to the C-terminal of which cysteine or a cysteine analogue is bound (1) A peptide consisting of the amino acid residues No. 1 to No. 28 from the N-terminal of SEQ ID NO:1, to the C-terminal of which homocysteine is bound (28AA-homocysteine)

(SEQ ID NO: 19)
N-terminal-DAEFRHDSGYEVHHQKLVFFAEDVGSNK<u>X</u>
(X: homocysteine)

(F) A peptide consisting of two or more of a peptide consisting of the amino acid sequence of SEQ ID NO:1 or a peptide consisting of a portion of the amino acid sequence of SEQ ID NO:1, to the C-terminal of which cysteine or a cysteine analogue is bound, wherein said two or more of the peptides are bound to each other via a disulfide bond between said cysteines or cysteine analogues (1) 28-Amino acid Aβ peptide with addition of cysteine (28AAC)

(SEQ ID NO: 20)
N-terminal-DAEFRHDSGYEVHHQKLVFFAEDVGSNK<u>C</u>

(2) 28-Amino acid Aβ peptide with addition of two cysteines (28AACC)

(SEQ ID NO: 21)
N-terminal-DAEFRHDSGYEVHHQKLVFFAEDVGSNK<u>CC</u>

A peptide consisting of 28AAC and 28AAC bound to each other via a disulfide bond (28AACdisulfide-28AAC), a peptide consisting of 28AAC and 28AACC bound to each other via a disulfide bond (28AACdisulfide-28AACC), a peptide consisting of 28AACC and 28AACC bound to each other via a disulfide bond (28AACCdisulfide-28AACC; including one with a disulfide bond formed between cysteines each at the N-terminal, one with a disulfide bond formed between cysteines each at the C-terminal, one with a disulfide bond formed between cysteine at the N-terminal and cysteine at the C-terminal, one with disulfide bonds each formed between cysteines each at the N-terminal and between cysteines each at the C-terminal, and one with disulfide bonds each formed between cysteine at the N-terminal and cysteine at the C-terminal), and a peptide consisting of plural 28AACC bound to each other via disulfide bonds (28AACC(28AAC)-bound product). FIG. 1 shows the structure of these peptides.

Among Aβ peptides with addition of insertion of cysteine as described above, a peptide consisting of Aβ peptide with a portion of its amino acid sequence being deleted with addition of cysteine such as 1-10·28-42AACys (SEQ ID NO:2), 1-10·28-41AACys (SEQ ID NO:3), 1-10·28-40AACys (SEQ ID NO:4), 1-10·28-39AACys (SEQ ID NO:5), 1-10·28-38AACys (SEQ ID NO:6), 1-10·28-37AACys (SEQ ID NO:7), 1-10·28-36AACys (SEQ ID NO:8), 1-9·28-37AACys (SEQ ID NO:9), 2-10·28-37AACys (SEQ ID NO:10) and 1-18·28-42AACys (SEQ ID NO:13); a peptide consisting of 28-amino acid Aβ peptide with addition or insertion of cysteine such as 1-18Cys19-28AACys (SEQ ID NO:16), 1-18Cys19-27AA (SEQ ID NO:14). 1-18Cys19-26AA (SEQ ID NO:15), 1-18Cys28-37AA (SEQ ID NO:17); a peptide consisting of 28-amino acid Aβ peptide with addition of homocysteine such as 28AA-homocysteine (SEQ ID NO:19); and 28AACdisulfide-28AAC and 28AACdisulfide-28AACC may induce a particularly enhanced immune reaction and thus may efficaciously be used for prophylaxis and treatment of Alzheimer disease.

According to the present invention, a peptide that may induce an enhanced immune response can be prepared by addition or insertion of cysteine or a cysteine analogue to a portion of an Aβ peptide or a sequence derived from an Aβ peptide. Whether a peptide obtained after addition or insertion of cysteine exerts an immune response-enhancing effect may be corroborated by immunization of mice with the peptide using the conventional techniques and determining an anti-Aβ IgG antibody titer in blood. Thus, the present invention also provides a method for enhancing an immune response characterized by that a peptide obtained by addition or insertion of cysteine or a cysteine analogue to a portion of an Aβ peptide or a sequence derived from an Aβ peptide is used.

A peptide preparation containing the peptide with addition of cysteine obtained by the present invention may be administered by any route of administration such as subcutaneous, transdermal, intramuscular, oral, or transnasal. Most preferably, it may be administered subcutaneously or intramuscularly.

While the immunogenic peptide with addition of cysteine of the present invention may provide sufficient immunization even if it is administered alone without an adjuvant, it may provide further sufficient immunization if in combination with an adjuvant. An adjuvant that may be used herein includes one that may preferably activate humoral immunity but may not stimulate cellular immunity, and typically an aluminum salt.

Moreover, a vector which comprises a gene fragment encoding a peptide that induce an enhanced immune response obtained by addition or insertion of cysteine or a cysteine analogue to a portion of an Aβ peptide or a sequence derived from an Aβ peptide may be used as a DNA vaccine for efficaciously preventing and treating Alzheimer disease. A nucleotide sequence encoding cysteine includes e.g. tgt but may be any sequence as far as it encodes cysteine. A gene fragment encoding the Aβ peptide consisting of the 42 amino acid residues mentioned above is described below. However, the nucleotide sequence described below represents a typical gene sequence of the Aβ peptide but any gene sequence may be employed insofar as it encodes the same amino acid sequence.

```
                                        (SEQ ID NO: 22)
gatgcagaat tccgacatga ctcaggatat gaagttcatc atcaaaaatt ggtgttcttt gcagaagatg tgggttcaaa caaaggtgca atcattggac tcatggtggg cggtgttgtc atagcg
```

An example of a gene fragment encoding a peptide obtained by addition or insertion of cysteine (Cys) to a portion of an Aβ peptide or a sequence derived from an Aβ peptide includes those described below. However, the nucleotide sequences described below represent a typical gene sequence encoding each of the peptides mentioned above but any gene sequence may be employed insofar as it encodes the same amino acid sequence.

```
A gene fragment encoding 1-10 • 28-42AACys
                                        (SEQ ID NO: 23)
gatgcagaat tccgacatga ctcaggatat aaaggtgcaa
tcattggact catggtgggc ggtgttgtca tagcgtgt A gene fragment encoding 1-10 • 28-41AACys
                                        (SEQ ID NO: 24)
gatgcagaat tccgacatga ctcaggatat aaaggtgcaa
tcattggact catggtgggc ggtgttgtca tatgt A gene fragment encoding 1-10 • 28-40AACys
                                        (SEQ ID NO: 25)
gatgcagaat tccgacatga ctcaggatat aaaggtgcaa
tcattggact catggtgggc ggtgttgtct gt A gene fragment encoding 1-10 • 28-39AACys
                                        (SEQ ID NO: 26)
gatgcagaat tccgacatga ctcaggatat aaaggtgcaa
tcattggact catggtgggc ggtgtttgt A gene fragment encoding 1-10 • 28-38AACys
                                        (SEQ ID NO: 27)
gatgcagaat tccgacatga ctcaggatat aaaggtgcaa
tcattggact catggtgggc ggttgt A gene fragment encoding 1-10 • 28-37AACys
                                        (SEQ ID NO: 28)
gatgcagaat tccgacatga ctcaggatat aaaggtgcaa
tcattggact catggtgggc tgt A gene fragment encoding 1-10 • 28-36AACys
                                        (SEQ ID NO: 29)
gatgcagaat tccgacatga ctcaggatat aaaggtgcaa
tcattggact catggtgtgt A gene fragment encoding 1-9 • 28-37AACys
                                        (SEQ ID NO: 30)
gatgcagaat tccgacatga ctcaggaaaa ggtgcaatca
ttggactcat ggtgggctgt A gene fragment encoding 2-10 • 28-37AACys
                                        (SEQ ID NO: 31)
gcagaattcc gacatgactc aggatataaa ggtgcaatca
ttggactcat ggtgggctgt A gene fragment encoding 3-10 • 28-37AACys
                                        (SEQ ID NO: 32)
gaattccgac atgactcagg atataaaggt gcaatcattg
gactcatggt gggctgt A gene fragment encoding 2-9 • 28-37AACys
                                        (SEQ ID NO: 33)
gcagaattcc gacatgactc aggaaaaggt gcaatcattg
gactcatggt gggctgt A gene fragment encoding 1-18 • 28-42AACys
                                        (SEQ ID NO: 34)
gatgcagaat tccgacatga ctcaggatat gaagttcatc
atcaaaaatt ggtgaaaggt gcaatcattg gactcatggt
gggcggtgtt gtcatagcgt gt A gene fragment encoding 1-18Cys19-27AA
                                        (SEQ ID NO: 35)
gatgcagaat tccgacatga ctcaggatat gaagttcatc
atcaaaaatt ggtgtgtttc tttgcagaag atgtgggttc aaac A gene fragment encoding 1-18Cys19-26AA
                                        (SEQ ID NO: 36)
gatgcagaat tccgacatga ctcaggatat gaagttcatc
atcaaaaatt ggtgtgtttc tttgcagaag atgtgggttc a A gene fragment encoding 1-18Cys19-28AACys
                                        (SEQ ID NO: 37)
gatgcagaat tccgacatga ctcaggatat gaagttcatc
atcaaaaatt ggtgtgtttc tttgcagaag atgtgggttc
aaacaaatgt A gene fragment encoding 1-18Cys28-37AA
                                        (SEQ ID NO: 38)
gatgcagaat tccgacatga ctcaggatat gaagttcatc
atcaaaaatt ggtgtgtaaa ggtgcaatca ttggactcat
ggtgggc A gene fragment encoding 1-18Cys28-37AACys
                                        (SEQ ID NO: 39)
gatgcagaat tccgacatga ctcaggatat gaagttcatc
atcaaaaatt ggtgtgtaaa ggtgcaatca ttggactcat
ggtgggctgt
```

The present invention is explained in more detail by means of the following Examples but should not be construed to be limited thereto.

EXAMPLE 1

Comparison of Antibody Inducing Ability Between Peptides Consisting of the Amino Acid Residues No. 1 to No. 10 of Aβ Peptide, to which Each of Various C-Terminal Peptides is Bound, to the C-terminal of which Cysteine is Added (1) Preparation of Aβ Peptides with Addition of Cysteine 1-10+30-42-amino acid Aβ peptide with addition of Cysteine (1-10·30-42AACys):

```
                                        (SEQ ID NO: 40)
N-terminal-DAEFRHDSGYAIIGLMVGGVVIAC
```

1-10+29-42-amino acid Aβ peptide with addition of Cysteine (1-10·29-42AACys):

(SEQ ID NO: 41)
N-terminal-DAEFRHDSGYGAIIGLMVGGVVIA<u>C</u>

1-10+28-42-amino acid Aβ peptide with addition of Cysteine (1-10·28-42AACys):

(SEQ ID NO: 2)
N-terminal-DAEFRHDSGYKGAIIGLMVGGVVIA<u>C</u>

1-10+28-42-amino acid Aβ peptide (1-10·28-42AA):

(SEQ ID NO: 42)
N-terminal-DAEFRHDSGYKGAIIGLMVGGVVIA

The above peptides were synthesized (Sigma Aldrich Japan) and diluted with saline to obtain a 5 mg/mL stock solution. To 100 µL of the stock solution was added 900 µL of saline to 0.5 mg/mL of the concentration and the mixture was dispensed into 1.5 mL tube (immunogen) and stored at −80° C. or lower till use.

(2) Immunized Mice

Male C57BL/6 mice (7 weeks old, SPF) were purchased from Japan Charles River Co., Ltd. and bred in SPF environment.

(3) Immunization Groups

The 16 mice were divided into 4 groups each comprising 4 mice: Group 1 administered with 1-10·30-42AACys; Group 2 administered with 1-10·29-42AACys; Group 3 administered with 1-10·28-42AACys and Group 4 administered with 1-10·28-42AA.

(4) Immunization and Schedule

Each 200 µL/mouse of an immunogen was administered to mice using a 1 mL tuberculin syringe (Terumo, SS-01T2613S) intradermally or subcutaneously at the abdomen (dose per mouse: 100 µg). The mice were immunized 3 times at 2-week intervals.

(5) Blood Sampling

On Day 7 from the final 3rd immunization, blood was collected from the abdominal aorta of all mice under anesthesia with pentobarbital sodium (Kyoritsu Seiyaku Corporation, Somnopentyl). The sampling blood was transferred to the Microtainer (Becton Dickinson Co., Ltd), adequate clotting has occurred at room temperature and then centrifuged at 5,000 rpm for 10 min. Each of the separated serum was dispensed into two 0.5 mL tubes and stored at −80° C. until measurement.

(6) Measurement of Anti-Aβ IgG Antibody

The Aβ peptide (1-40 amino acid sequence: N-terminal-DAEFRHDSGYEVHHQKLVFFAEDVGSNK-GAIIGLMVGGVV (SEQ ID NO: 43) synthesized by Hokkaido System Science Co., Ltd.), diluted to 10 µg/mL with 0.1M carbonate buffer, pH9.6, was added to 8-well strips (Nalge Nunc K.K., Immobilizer Amino) at 100 µL/well and left to incubate at 4° C. overnight for immobilization. On the following day, each well was washed 3 times with 300 µL of PBS containing 0.05% Tween20 (PEST), added with 10 mM ethanolamine at 300 µL/well and left to incubate at room temperature for 1 hour.

After 1 hour, the 10 mM ethanolamine was fully removed and a specimen diluted with PEST by 50- to 10000-fold was added to each well at 100 µL/well. After reaction at room temperature for 1 hour, the diluted serum added was discarded and each well was washed 3 times with 300 µL/well of PEST. After washing, the wash solution in the well was fully removed, an HRP-labeled anti-mouse IgG goat antibody (American Curlex, A131PS) diluted with the solution for the specimen dilution by 2000-fold was added at 100 µL/well followed by reaction at room temperature for 1 hour. After the reaction, the solution for labeled antibody dilution was discarded and each well was washed twice with 300 µL/well of PEST and twice with the equivalent amount of distilled water, to which 100 µL/well of a chromogenic substrate solution TMB+ (Dako Inc.) was added followed by reaction at room temperature for 30 min. under shading. Then, 100 µL/well of 1N sulfuric acid was added to quench development and optical density at 450 nm (OD450 value) was measured.

A commercially available monoclonal antibody to Aβ (CHEMI-CON Corporation, MAB1560) was used as standard serum. The standard serum was diluted with PBST to 0.156, 0.3125, 0.625, 1.25, 2.5, 5, 10 ng/mL to prepare standards for the antibody titer measurement. An anti-Aβ IgG antibody of each murine serum specimen was determined and simultaneously the OD450 value of each diluted specimen was measured. An anti-Aβ IgG antibody titer of each murine serum specimen was calculated using the unit of the resulting standards and the standard curve of the OD450 value.

Table 1 shows the calculated anti-Aβ antibody titer of the murine serum in each of the immunization groups. As shown in Table 1, induction of an antibody to Aβ was observed in the group administered with 1-10·28-42AACys and in the group administered with 1-10·28-42AA. Also, as compared to the immunization with Aβ peptide fragments without addition of cysteine (1-10·28-42AA), the immunization with Aβ peptide fragments with addition of cysteine (1-10·28-42AACys) provided a higher antibody titer against Aβ.

TABLE 1

| Group | Antibody titer(ng/mL) | | | | |
| | Animal No. | | | | |
| | 1 | 2 | 3 | 4 | Mean |
| 1-10•30-42AACys | 9 | 7 | 11 | 8 | 8.4 |
| 1-10•29-42AACys | 16 | 16 | 87 | 11 | 32.6 |
| 1-10•28-42AACys | 46266 | 19854 | 40681 | 33 | 26708.6 |
| 1-10•28-42AA | 66 | 715 | 3559 | 13 | 1088.5 |

EXAMPLE 2

Comparison of Antibody Inducing Ability Between Peptides Consisting of the Amino Acid Residues No. 1 to No. 10 of Aβ Peptide, to which Each of the Sequences of the Amino Acid Residues No. 28 to No. 42, No. 28 to No. 41, No. 28 to No. 40, No. 28 to No. 39, No. 28 to No. 38, No. 28 to No. 37, No. 28 to No. 36, No. 28 to No. 35, and No. 28 to No. 34 of Aβ Peptide is Bound, to the C-terminal of which Cysteine is Added (1) Preparation of Aβ Peptides with Addition of Cysteine 1-10+28-42-amino acid Aβ peptide with addition of Cysteine (1-10·28-42AACys):

(SEQ ID NO: 2)
N-terminal-DAEFRHDSGYKGAIIGLMVGGVVIA<u>C</u>

1-10+28-41-amino acid Aβ peptide with addition of Cysteine (1-10·28-41AACys):

N-terminal-DAEFRHDSGYKGAIIGLMVGGVVIC (SEQ ID NO: 3)

1-10+28-40-amino acid Aβ peptide with addition of Cysteine (1-10·28-40AACys):

N-terminal-DAEFRHDSGYKGAIIGLMVGGVVC (SEQ ID NO: 4)

1-10+28-39-amino acid Aβ peptide with addition of Cysteine (1-10·28-39AACys):

N-terminal-DAEFRHDSGYKGAIIGLMVGGVC (SEQ ID NO: 5)

1-10+28-38-amino acid Aβ peptide with addition of Cysteine (1-10·28-38AACys):

N-terminal-DAEFRHDSGYKGAIIGLMVGGC (SEQ ID NO: 6)

1-10+28-37-amino acid Aβ peptide with addition of Cysteine (1-10·28-37AACys):

N-terminal-DAEFRHDSGYKGAIIGLMVGC (SEQ ID NO: 7)

1-10+28-36-amino acid Aβ peptide with addition of Cysteine (1-10·28-36AACys):

N-terminal-DAEFRHDSGYKGAIIGLMVC (SEQ ID NO: 8)

1-10+28-35-amino acid Aβ peptide with addition of Cysteine (1-10·28-35AACys):

N-terminal-DAEFRHDSGYKGAIIGLMC (SEQ ID NO: 44)

1-10+28-34-amino acid Aβ peptide with addition of Cysteine (1-10·28-34AACys):

N-terminal-DAEFRHDSGYKGAIIGLC (SEQ ID NO: 45)

The above peptides were synthesized (Sigma Aldrich Japan) and diluted with saline to obtain a 5 mg/mL stock solution. To 100 µL of the stock solution was added 900 µL of saline to 0.5 mg/mL of the concentration and the mixture was dispensed into 1.5 mL tube (immunogen) and stored at −80° C. or lower till use.

(2) Immunized Mice

Male C57BL/6 mice (7 weeks old, SPF) were purchased from Japan Charles River Co., Ltd. and bred in SPF environment.

(3) Immunization Groups

The 36 mice were divided into 9 groups each comprising 4 mice: Group 1 administered with 1-10·28-42AACys, Group 2 administered with 1-10·28-41AACys, Group 3 administered with 1-10·28-40AACys, Group 4 administered with 1-10·28-39AACys, Group 5 administered with 1-10·28-38AACys, Group 6 administered with 1-10·28-37AACys, Group 7 administered with 1-10·28-36AACys, Group 8 administered with 1-10·28-35AACys and Group 9 administered with 1-10·28-34AACys.

(4) Immunization and Schedule

Each 200 µL/mouse of an immunogen was administered to mice using a 1 mL tuberculin syringe (Terumo, SS-01T2613S) intradermally or subcutaneously at the abdomen (dose per mouse: 100 µg). The mice were immunized 3 times at 2-week intervals.

(5) Blood Sampling

On Day 7 from the final 3rd immunization, blood was collected from the abdominal aorta of all mice under anesthesia with pentobarbital sodium (Kyoritsu Seiyaku Corporation, Somnopentyl). The sampling blood was transferred to the Microtainer (Becton Dickinson Co., Ltd), adequate clotting has occurred at room temperature and then centrifuged at 5,000 rpm for 10 min. Each of the separated serum was dispensed into two 0.5 mL tubes and stored at −80° C. until measurement.

(6) Measurement of Anti-Aβ IgG Antibody

Measurement of anti-Aβ IgG antibody was performed as described above. Table 2 shows the calculated anti-Aβ antibody titer of the murine serum in each of the immunization groups. As shown in Table 2, induction of an antibody to Aβ was observed in 1-10·28-42AACys, 1-10·28-41AACys, 1-10·28-40AACys, 1-10·28-39AACys, 1-10·28-38AACys, 1-10·28-37AACys and 1-10·28-36AACys.

TABLE 2

| | Antibody titer (ng/mL) | | | | |
| | Animal No. | | | | |
| Group | 1 | 2 | 3 | 4 | Mean |
|---|---|---|---|---|---|
| 1-10·28-42AACys | 32 | 30482 | 33623 | 2072 | 16552.3 |
| 1-10·28-41AACys | 292 | 1000 | 48460 | 422012 | 117941.1 |
| 1-10·28-40AACys | 4560 | 148622 | 5118 | 4988 | 40822.0 |
| 1-10·28-39AACys | 139361 | 10808 | 13326 | 230453 | 98487.0 |
| 1-10·28-38AACys | 19149 | 34270 | 108780 | 61824 | 56005.8 |
| 1-10·28-37AACys | 79708 | 1531 | 24694 | 100619 | 51638.0 |
| 1-10·28-36AACys | 11821 | 259763 | 77 | 44922 | 79145.6 |
| 1-10·28-35AACys | 44 | 19 | 8361 | 220 | 2161.0 |
| 1-10·28-34AACys | 29 | 30 | 26 | 25 | 27.4 |

EXAMPLE 3

Comparison of Antibody Inducing Ability Between Peptides Consisting of Each of Various N-terminal Peptides of Aβ Peptide, to Which the Amino Acid Residues No. 28 to No. 37 of Aβ Peptide is Bound, to the C-terminal of Which Cysteine is Added (1) Preparation of Aβ Peptides with Addition of Cysteine 1-9+28-37-amino acid Aβ peptide with addition of Cysteine (1-9·28-37AACys):

N-terminal-DAEFRHDSGKGAIIGLMVGC (SEQ ID NO: 9)

1-8+28-37-amino acid Aβ peptide with addition of Cysteine (1-8·28-37AACys):

N-terminal-DAEFRHDSKGAIIGLMVGC (SEQ ID NO: 46)

1-7+28-37-amino acid Aβ peptide with addition of Cysteine (1-7·28-37AACys):

(SEQ ID NO: 47)
N-terminal-DAEFRHDKGAIIGLMVGC

The above peptides were synthesized (Sigma Aldrich Japan) and diluted with saline to obtain a 5 mg/mL stock solution. To 100 μL of the stock solution was added 900 μL of saline to 0.5 mg/mL of the concentration and the mixture was dispensed into 1.5 mL tube (immunogen) and stored at −80° C. or lower till use.

(2) Immunized Mice

Male C57BL/6 mice (7 weeks old, SPF) were purchased from Japan Charles River Co., Ltd. and bred in SPF environment.

(3) Immunization Groups

The 12 mice were divided into 3 groups each comprising 4 mice: Group 1 administered with 1-9·28-37AACys, Group 2 administered with 1-8·28-37AACys and Group 3 administered with 1-7·28-37AACys.

(4) Immunization and Schedule

Each 200 μL/mouse of an immunogen was administered to mice using a 1 mL tuberculin syringe (Terumo, SS-01T2613S) intradermally or subcutaneously at the abdomen (dose per mouse: 100 μg). The mice were immunized 3 times at 2-week intervals.

(5) Blood Sampling

On Day 7 from the final 3rd immunization, blood was collected from the abdominal aorta of all mice under anesthesia with pentobarbital sodium (Kyoritsu Seiyaku Corporation, Somnopentyl). The sampling blood was transferred to the Microtainer (Becton Dickinson Co., Ltd), adequate clotting has occurred at room temperature and then centrifuged at 5,000 rpm for 10 min. Each of the separated serum was dispensed into two 0.5 mL tubes and stored at −80° C. until measurement.

(6) Measurement of Anti-Aβ IgG Antibody

Measurement of anti-Aβ IgG antibody was performed as described above. Table 3 shows the calculated anti-Aβ antibody titer of the murine serum in each of the immunization groups. As shown in Table 3, induction of an antibody to Aβ was observed in 1-9·28-37AACys peptide.

TABLE 3

| | Antibody titer(ng/mL) | | | | |
| --- | --- | --- | --- | --- | --- |
| | Animal No. | | | | |
| Group | 1 | 2 | 3 | 4 | Mean |
| 1-9·28-37AACys | 398 | 249 | 2772 | 8899 | 3079.5 |
| 1-8·28-37AACys | 16 | 16 | 43 | 31 | 26.4 |
| 1-7·28-37AACys | 26 | 27 | 34 | 15 | 25.6 |

EXAMPLE 4

Comparison of Antibody Inducing Ability Between Peptides Consisting of the Amino Acid Residues No. 2 to No. 10 or No. 3 to No. 10 or No. 4 to No. 10 of Aβ Peptide, to which the Amino Acid Residues No. 28 to No. 37 of Aβ Peptide is Bound, to the C-terminal of which Cysteine is Added (1) Preparation of Aβ Peptides with Addition of Cysteine
2-10+28-37-amino acid Aβ peptide with addition of Cysteine (2-10·28-37AACys):

(SEQ ID NO: 10)
N-terminal-AEFRHDSGYKGAIIGLMVGC 3-10+28-37-amino acid Aβ peptide with addition of Cysteine (3-10·28-37AACys):

(SEQ ID NO: 11)
N-terminal-EFRHDSGYKGAIIGLMVGC 4-10+28-37-amino acid Aβ peptide with addition of Cysteine (4-10·28-37AACys):

(SEQ ID NO: 48)
N-terminal-FRHDSGYKGAIIGLMVGC 2-9+28-37-amino acid Aβ peptide with addition of Cysteine (2-9·28-37AACys):

(SEQ ID NO: 12)
N-terminal-AEFRHDSGKGAIIGLMVGC

The above peptides were synthesized (Sigma Aldrich Japan) and diluted with saline to obtain a 5 mg/mL stock solution. To 100 μL of the stock solution was added 900 μL of saline to 0.5 mg/mL of the concentration and the mixture was dispensed into 1.5 mL tube (immunogen) and stored at −80° C. or lower till use.

(2) Immunized Mice

Male C57BL/6 mice (7 weeks old, SPF) were purchased from Japan Charles River Co., Ltd. and bred in SPF environment.

(3) Immunization Groups

The 16 mice were divided into 4 groups each comprising 4 mice: Group 1 administered with 2-10·28-37AACys, Group 2 administered with 3-10·28-37AACys, Group administered with 4-10·28-37AACys and Group 4 administered with 2-9·28-37AACys.

(4) Immunization and Schedule

Each 200 μL/mouse of an immunogen was administered to mice using a 1 mL tuberculin syringe (Terumo, SS-01T2613S) intradermally or subcutaneously at the abdomen (dose per mouse: 100 μg). The mice were immunized 3 times at 2-week intervals.

(5) Blood Sampling

On Day 7 from the final 3rd immunization, blood was collected from the abdominal aorta of all mice under anesthesia with pentobarbital sodium (Kyoritsu Seiyaku Corporation, Somnopentyl). The sampling blood was transferred to the Microtainer (Becton Dickinson Co., Ltd), adequate clotting has occurred at room temperature and then centrifuged at 5,000 rpm for 10 min. Each of the separated serum was dispensed into two 0.5 mL tubes and stored at −80° C. until measurement.

(6) Measurement of Anti-Aβ IgG Antibody

Measurement of anti-Aβ IgG antibody was performed as described above. Table 4 shows the calculated anti-Aβ antibody titer of the murine serum in each of the immunization groups. As shown in Table 4, induction of an antibody to Aβ was observed in 2-10·28-37AACys, 3-10·28-37AACys and 2-9·28-37AACys peptides.

TABLE 4

| | Antibody titer (ng/mL) | | | | |
| --- | --- | --- | --- | --- | --- |
| | Animal No. | | | | |
| Group | 1 | 2 | 3 | 4 | Mean |
| 2-10•28-37AACys | 72890 | 57573 | 6094 | 42593 | 44787.5 |
| 3-10•28-37AACys | 3203 | 1456 | 4500 | 52 | 2302.8 |
| 4-10•28-37AACys | 24 | 31 | 53 | 27 | 33.8 |
| 2-9•28-37AACys | 7038 | 29489 | 16 | 17 | 9139.9 |

EXAMPLE 5

Comparison of Antibody Inducing Ability Between Peptide Consisting of the Amino Acid Residues No. 1 to No. 10, to which the Amino Acid Residues No. 28 to No. 42 of Aβ Peptide is Bound, to the C-terminal of which Cysteine is Added, and Peptide Consisting of the Amino Acid Residues No. 1 to No. 18, to which the Amino Acid Residues No. 28 to No. 42 of Aβ Peptide is Bound, to the C-terminal of which Cysteine is Added (1) Preparation of Aβ Peptides with Addition of Cysteine 1-18+28-42-amino acid Aβ peptide with addition of Cysteine (1-18·28-42AACys):

(SEQ ID NO: 13)
N-terminal-DAEFRHDSGYEVHHQKLVKGAIIGLMVGGVVIA<u>C</u>

1-10+28-42-amino acid Aβ peptide with addition of Cysteine (1-10·28-42AACys):

(SEQ ID NO: 2)
N-terminal-DAEFRHDSGYKGAIIGLMVGGVVIA<u>C</u>

The above peptides were synthesized (Sigma Aldrich Japan) and diluted with saline to obtain a 5 mg/mL stock solution. To 100 μL of the stock solution was added 900 μL of saline to 0.5 mg/mL of the concentration and the mixture was dispensed into 1.5 mL tube (immunogen) and stored at −80° C. or lower till use.

(2) Immunized Mice

Male C57BL/6 mice (7 weeks old, SPF) were purchased from Japan Charles River Co., Ltd. and bred in SPF environment.

(3) Immunization Groups

The 8 mice were divided into 2 groups each comprising 4 mice: Group 1 administered with 1-18·28-42AACys and Group 2 administered with 1-10.28-42AACys.

(4) Immunization and Schedule

Each 200 μL/mouse of an immunogen was administered to mice using a 1 mL tuberculin syringe (Terumo, SS-01T2613S) intradermally or subcutaneously at the abdomen (dose per mouse: 100 μg). The mice were immunized 3 times at 2-week intervals.

(5) Blood Sampling

On Day 7 from the final 3rd immunization, blood was collected from the abdominal aorta of all mice under anesthesia with pentobarbital sodium (Kyoritsu Seiyaku Corporation, Somnopentyl). The sampling blood was transferred to the Microtainer (Becton Dickinson Co., Ltd), adequate clotting has occurred at room temperature and then centrifuged at 5,000 rpm for 10 min. Each of the separated serum was dispensed into two 0.5 mL tubes and stored at −80° C. until measurement.

(6) Measurement of Anti-Aβ IgG Antibody

Measurement of anti-Aβ IgG antibody was performed as described above. Table 5 shows the calculated anti-Aβ antibody titer of the murine serum in each of the immunization groups. As shown in Table 5, similar induction of an antibody to Aβ was observed in both the group administered with 1-18·28-42AACys and the group administered with 1-10·28-42AACys.

TABLE 5

| | Antibody titer(ng/mL) | | | | |
| --- | --- | --- | --- | --- | --- |
| | Animal No. | | | | |
| Group | 1 | 2 | 3 | 4 | Mean |
| 1-18•28-42AACys | 69336 | 41211 | 51611 | 7004 | 42290.5 |
| 1-10•28-42AACys | 886.2 | 463379 | 414.8 | 3314 | 116998.5 |

EXAMPLE 6

Comparison of Antibody Inducing Ability Between Peptide Consisting of Aβ Peptide Wherein Cysteine is Inserted Between the Amino Acid Residues Nos. 18 and 19 of Aβ Peptide and Said Peptide, to the C-terminal of which Cysteine is Bound a peptide consisting of 28-amino acid Aβ peptide wherein cysteine is inserted between the amino acid residues Nos. 18 and 19 of Aβ peptide (1-18Cys19-28AA):

(SEQ ID NO: 49)
N-terminal-DAEFRHDSGYEVHHQKLV<u>C</u>FFAEDVGSNK a peptide consisting of 28-amino acid Aβ peptide wherein cysteine is inserted between the amino acid residues Nos. 18 and 19 of Aβ peptide, to the C-terminal of which cysteine is bound (1-18Cys19-28AACys):

(SEQ ID NO: 16)
N-terminal-DAEFRHDSGYEVHHQKLV<u>C</u>FFAEDVGSNK<u>C</u>

The above peptides were synthesized (Sigma Aldrich Japan) and diluted with saline to obtain a 5 mg/mL stock solution. To 100 μL of the stock solution was added 900 μL of saline to 0.5 mg/mL of the concentration and the mixture was dispensed into 1.5 mL tube (immunogen) and stored at −80° C. or lower till use.

(2) Immunized Mice

Male C57BL/6 mice (7 weeks old, SPF) were purchased from Japan Charles River Co., Ltd. and bred in SPF environment.

(3) Immunization Groups

The 8 mice were divided into 2 groups each comprising 4 mice: Group 1 administered with 1-18Cys19-28AA and Group 2 administered with 1-18Cys19-28AACys.

(4) Immunization and Schedule

Each 200 μL/mouse of an immunogen was administered to mice using a 1 mL tuberculin syringe (Terumo, SS-01T2613S) intradermally or subcutaneously at the abdomen (dose per mouse: 100 μg). The mice were immunized 3 times at 2-week intervals.

(5) Blood Sampling

On Day 7 from the final 3rd immunization, blood was collected from the abdominal aorta of all mice under anesthesia with pentobarbital sodium (Kyoritsu Seiyaku Corporation, Somnopentyl). The sampling blood was transferred to the Microtainer (Becton Dickinson Co., Ltd), adequate clotting has occurred at room temperature and then centrifuged at 5,000 rpm for 10 min. Each of the separated serum was dispensed into two 0.5 mL tubes and stored at −80° C. until measurement.

(6) Measurement of Anti-Aβ IgG Antibody

Measurement of anti-Aβ IgG antibody was performed as described above. Table 6 shows the calculated anti-Aβ antibody titer of the murine serum in each of the immunization groups. As shown in Table 6, similar induction of an antibody to Aβ was observed in both the group administered with 1-18Cys19-28AA and the group administered with 1-18Cys19-28AACys.

TABLE 6

| | Antibody titer(ng/mL) | | | | |
|---|---|---|---|---|---|
| | Animal No. | | | | |
| Group | 1 | 2 | 3 | 4 | Mean |
| 1-18Cys19-28AA | 448154 | 97146 | 233411 | 57794 | 209126.3 |
| 1-18Cys19-28AACys | 19908 | 361259 | 4161 | 29412 | 103685.0 |

EXAMPLE 7

Evaluation of Antibody Induction in 25-amino acid Aβ Peptide, 26-amino acid Aβ Peptide and 27-amino acid Aβ Peptide, Wherein Cysteine is Inserted Between the Amino Acid Residues Nos. 18 and 19 of Said Aβ Peptides (1) Preparation of Aβ Peptides with Addition of Cysteine
 27-amino acid Aβ peptide wherein cysteine is inserted between the amino acid residues Nos. 18 and 19 (1-18Cys19-27AA):

(SEQ ID NO: 14)
N-terminal-DAEFRHDSGYEVHHQKLVCFFAEDVGSN 26-amino acid Aβ peptide wherein cysteine is inserted between the amino acid residues Nos. 18 and 19 (1-18Cys19-26AA):

(SEQ ID NO: 15)
N-terminal-DAEFRHDSGYEVHHQKLVCFFAEDVGS 25-amino acid Aβ peptide wherein cysteine is inserted between the amino acid residues Nos. 18 and 19 (1-18Cys19-25AA):

(SEQ ID NO: 50)
N-terminal-DAEFRHDSGYEVHHQKLVCFFAEDVG

The above peptides were synthesized (Sigma Aldrich Japan) and diluted with saline to obtain a 5 mg/mL stock solution. To 100 μL of the stock solution was added 900 μL of saline to 0.5 mg/mL of the concentration and the mixture was dispensed into 1.5 mL tube (immunogen) and stored at −80° C. or lower till use.

(2) Immunized Mice

Male C57BL/6 mice (7 weeks old, SPF) were purchased from Japan Charles River Co., Ltd. and bred in SPF environment.

(3) Immunization Groups

The 12 mice were divided into 3 groups each comprising 4 mice: Group 1 administered with 1-18Cys19-27AA, Group 2 administered with 1-18Cys19-26AA and Group 3 administered with 1-18Cys19-25AA.

(4) Immunization and Schedule

Each 200 μL/mouse of an immunogen was administered to mice using a 1 mL tuberculin syringe (Terumo, SS-01T2613S) intradermally or subcutaneously at the abdomen (dose per mouse: 100 μg). The mice were immunized 3 times at 2-week intervals.

(5) Blood Sampling

On Day 7 from the final 3rd immunization, blood was collected from the abdominal aorta of all mice under anesthesia with pentobarbital sodium (Kyoritsu Seiyaku Corporation, Somnopentyl). The sampling blood was transferred to the Microtainer (Becton Dickinson Co., Ltd), adequate clotting has occurred at room temperature and then centrifuged at 5,000 rpm for 10 min. Each of the separated serum was dispensed into two 0.5 mL tubes and stored at −80° C. until measurement.

(6) Measurement of Anti-Aβ IgG Antibody

Measurement of anti-Aβ IgG antibody was performed as described above. Table 7 shows the calculated anti-Aβ antibody titer of the murine serum in each of the immunization groups. As shown in Table 7, induction of an antibody to Aβ was observed in the group administered with 1-18Cys19-27AA and in the group administered with 1-18Cys19-26AA. In the group administered with 1-18Cys19-25AA, induction of an antibody to Aβ was observed in one of four cases.

TABLE 7

| | Antibody titer(ng/mL) | | | | |
|---|---|---|---|---|---|
| | Animal No. | | | | |
| Group | 1 | 2 | 3 | 4 | Mean |
| 1-18Cys19-27AA | 2482 | 3125 | 2631 | 17.2 | 2063.8 |
| 1-18Cys19-26AA | 127.5 | 7001 | 15779 | 164 | 5767.9 |
| 1-18Cys19-25AA | 1.5 | 6.6 | 71.4 | 1398 | 369.4 |

EXAMPLE 8

Evaluation of Antibody Induction in Peptides Consisting of The Amino Acid Residues No. 1 to No. 18 of Aβ Peptide, to which the Amino Acid Residues No. 28 to No. 37 of Aβ Peptide is Bound, with Addition of Cysteine (1) Preparation of Aβ Peptides with Addition of Cysteine
 a peptide consisting of the amino acid residues No. 1 to No. 18 of Aβ peptide, to the C-terminal of which cysteine is bound, to which a sequence consisting of the amino acid residues No. 28 to No. 37 of Aβ peptide is further bound (1-18Cys28-37AA):

(SEQ ID NO: 17)
N-terminal-DAEFRHDSGYEVHHQKLVCKGAIIGLMVG a peptide consisting of the amino acid residues No. 1 to No. 18 of Aβ peptide, to the C-terminal of which cysteine is bound, to which a sequence consisting of the amino acid residues No. 28 to No. 37 of Aβ peptide is further bound, to the C-terminal of which cysteine is bound (1-18Cys28-37AACys):

(SEQ ID NO: 18)
N-terminal-DAEFRHDSGYEVHHQKLVCKGAIIGLMVGC a peptide consisting of the amino acid residues No. 1 to No. 18 of Aβ peptide, to which a sequence consisting of the amino acid residues No. 28 to No. 37 of Aβ peptide is further bound, to the C-terminal of which cysteine is bound (1-18·28-37AACys):

```
                                          (SEQ ID NO: 51)
N-terminal-DAEFRHDSGYEVHHQKLVKGAIIGLMVGC
``` a peptide consisting of the amino acid residues No. 1 to No. 18 of Aβ peptide, to which a sequence consisting of the amino acid residues No. 28 to No. 37 of Aβ peptide is further bound (1-18·28-37AA):

```
                                          (SEQ ID NO: 52)
N-terminal-DAEFRHDSGYEVHHQKLVKGAIIGLMVG
```

The above peptides were synthesized (Sigma Aldrich Japan) and diluted with saline to obtain a 5 mg/mL stock solution. To 100 μL of the stock solution was added 900 μL of saline to 0.5 mg/mL of the concentration and the mixture was dispensed into 1.5 mL tube (immunogen) and stored at −80° C. or lower till use.

(2) Immunized Mice

Male C57BL/6 mice (7 weeks old, SPF) were purchased from Japan Charles River Co., Ltd. and bred in SPF environment.

(3) Immunization Groups

The 16 mice were divided into 4 groups each comprising 4 mice: Group 1 administered with 1-18Cys28-37AA, Group 2 administered with 1-18Cys28-37AACys, Group 3 administered with 1-18·28-37AACys and Group 4 administered with 1-18·28-37AA.

(4) Immunization and Schedule

Each 200 μL/mouse of an immunogen was administered to mice using a 1 mL tuberculin syringe (Terumo, SS-01T2613S) intradermally or subcutaneously at the abdomen (dose per mouse: 100 μg). The mice were immunized 3 times at 2-week intervals.

(5) Blood Sampling

On Day 7 from the final 3rd immunization, blood was collected from the abdominal aorta of all mice under anesthesia with pentobarbital sodium (Kyoritsu Seiyaku Corporation, Somnopentyl). The sampling blood was transferred to the Microtainer (Becton Dickinson Co., Ltd), adequate clotting has occurred at room temperature and then centrifuged at 5,000 rpm for 10 min. Each of the separated serum was dispensed into two 0.5 mL tubes and stored at −80° C. until measurement.

(6) Measurement of Anti-Aβ IgG Antibody

Measurement of anti-Aβ IgG antibody was performed as described above. Table 8 shows the calculated anti-Aβ antibody titer of the murine serum in each of the immunization groups. As shown in Table 8, induction of an antibody to Aβ was observed in the group administered with 1-18Cys28-37AA and in the group administered with 1-18Cys28-37AA-Cys.

TABLE 8

| Group | Antibody titer(ng/mL) | | | | |
|---|---|---|---|---|---|
| | Animal No. | | | | |
| | 1 | 2 | 3 | 4 | Mean |
| 1-18Cys28-37AA | 12541 | 1964 | 599 | 25102 | 10051.5 |
| 1-18Cys28-37AACys | 1073 | 43 | 10 | 4864 | 1497.5 |
| 1-18•28-37AACys | 11 | 9 | 10 | 13 | 10.75 |
| 1-18•28-37AA | 11 | 11 | 11 | 9 | 10.5 |

EXAMPLE 9

Evaluation of Antibody Induction in Peptides Consisting of 28-Amino Acid Aβ Peptide with Addition of Homocysteine, a Precursor of Cysteine, and of Glutathione, a Metabolite of Cysteine (1) Preparation of Aβ Peptides with Addition of Precursor or Metabolite of Cysteine a peptide consisting of 28-amino acid Aβ peptide with addition of homocysteine (28AA-homocysteine):

```
                                          (SEQ ID NO: 19)
N-terminal-DAEFRHDSGYEVHHQKLVFFAEDVGSNK-
Homocysteine
``` a peptide consisting of 28-amino acid Aβ peptide with addition of glutathione (28AA-glutathione):

```
                                          (SEQ ID NO: 53)
N-terminal-DAEFRHDSGYEVHHQKLVFFAEDVGSNK-
Glutathione
```

The above peptides were synthesized (Sigma Aldrich Japan) and diluted with saline to obtain a 5 mg/mL stock solution. To 100 μL of the stock solution was added 900 μL of saline to 0.5 mg/mL of the concentration and the mixture was dispensed into 1.5 mL tube (immunogen) and stored at −80° C. or lower till use.

(2) Immunized Mice

Male C57BL/6 mice (7 weeks old, SPF) were purchased from Japan Charles River Co., Ltd. and bred in SPF environment.

(3) Immunization Groups

The 8 mice were divided into 2 groups each comprising 4 mice: Group 1 administered with 28AA-homocysteine and Group 2 administered with 28AA-glutathione.

(4) Immunization and Schedule

Each 200 μL/mouse of an immunogen was administered to mice using a 1 mL tuberculin syringe (Terumo, SS-01T2613S) intradermally or subcutaneously at the abdomen (dose per mouse: 100 μg). The mice were immunized 3 times at 2-week intervals.

(5) Blood Sampling

On Day 7 from the final 3rd immunization, blood was collected from the abdominal aorta of all mice under anesthesia with pentobarbital sodium (Kyoritsu Seiyaku Corporation, Somnopentyl). The sampling blood was transferred to the Microtainer (Becton Dickinson Co., Ltd), adequate clotting has occurred at room temperature and then centrifuged at 5,000 rpm for 10 min. Each of the separated serum was dispensed into two 0.5 mL tubes and stored at −80° C. until measurement.

(6) Measurement of Anti-Aβ IgG Antibody

Measurement of anti-Aβ IgG antibody was performed as described above. Table 9 shows the calculated anti-Aβ antibody titer of the murine serum in each of the immunization groups. As shown in Table 9, induction of an antibody to Aβ was observed in the group administered with 28AA-homocysteine.

TABLE 9

| Group | Antibody titer(ng/mL) Animal No. | | | | |
| --- | --- | --- | --- | --- | --- |
| | 1 | 2 | 3 | 4 | Mean |
| 28AA-Homocysteine | 178 | 10525 | 4975 | 35154 | 12708 |
| 28AA-Glutathione | 150 | 134 | 133 | 146 | 141 |

EXAMPLE 10

Evaluation of Antibody Induction in Peptides Consisting of 28-amino acid Aβ Peptide with Addition of Cysteine that Formed Disulfide Bond (1) Preparation of Aβ Peptides with Addition of Cysteine
  a peptide consisting of 28-amino acid Aβ peptide with addition of cysteine (28AAC):

```
                                        (SEQ ID NO: 20)
N-terminal-DAEFRHDSGYEVHHQKLVFFAEDVGSNK-C
``` a peptide consisting of 28-amino acid Aβ peptide with addition of two cysteines (28AACC):

```
                                        (SEQ ID NO: 21)
N-terminal-DAEFRHDSGYEVHHQKLVFFAEDVGSNK-CC
```

(2) Preparation of Peptides Consisting of 28-amino acid Aβ Peptide with Addition of Cysteine that Formed Disulfide Bond A peptide consisting of 28AAC and 28AAC bound to each other via disulfide bond (28AACdisulfide28AAC) and a peptide consisting of 28AAC and 28AACC bound to each other via disulfide bond (28AACdisulfide28AACC) were prepared. The obtained peptides had the structure that the two peptides are bound to each other with cysteines at the C-terminal via disulfide bond, or the structures that a dimer comprising N-terminal-DAEFRHDSGYEVHHQKLVFFAEDVGSNK-CC (SEQ ID NO: 21) is further subject to disulfide bonds to form a trimer and a polymer (FIG. 1).

(2) Immunized Mice

Male C57BL/6 mice (7 weeks old, SPF) were purchased from Japan Charles River Co., Ltd. and bred in SPF environment.

(3) Immunization Groups

The 8 mice were divided into 2 groups each comprising 4 mice: Group 1 administered with 28AACdisulfide-28AAC and Group 2 administered with 228AACdisulfide-28AACC.

(4) Immunization and Schedule

Each 200 μL/mouse of an immunogen was administered to mice using a 1 mL tuberculin syringe (Terumo, SS-01T2613S) intradermally or subcutaneously at the abdomen (dose per mouse: 100 μg). The mice were immunized 3 times at 2-week intervals.

(5) Blood Sampling

On Day 7 from the final 3rd immunization, blood was collected from the abdominal aorta of all mice under anesthesia with pentobarbital sodium (Kyoritsu Seiyaku Corporation, Somnopentyl). The sampling blood was transferred to the Microtainer (Becton Dickinson Co., Ltd), adequate clotting has occurred at room temperature and then centrifuged at 5,000 rpm for 10 min. Each of the separated serum was dispensed into two 0.5 mL tubes and stored at −80° C. until measurement.

(6) Measurement of Anti-Aβ IgG Antibody

Measurement of anti-Aβ IgG antibody was performed as described above. Table 10 shows the calculated anti-Aβ antibody titer of the murine serum in each of the immunization groups. As shown in Table 10, for peptides consisting of 28-amino acid Aβ peptide with addition of cysteine that formed disulfide bond, induction of an antibody to Aβ was observed in both the group administered with 28AACdisulfide-28AAC and the group administered with 228AACdisulfide-28AACC.

TABLE 10

| Group | Antibody titer(ng/mL) Animal No. | | | | |
| --- | --- | --- | --- | --- | --- |
| | 1 | 2 | 3 | 4 | Mean |
| 28AAC disulfide 28AAC | 244 | 2428 | 770668 | 6683 | 195005.7 |
| 28AAC disulfide 28AACC | 2110 | 136610 | 49129 | 1058945 | 311698.6 |

INDUSTRIAL APPLICABILITY

A method for enhancing an immune response characterized by that a peptide obtained by addition or insertion of cysteine or a cysteine analogue to an Aβ peptide or a sequence derived from an Aβ peptide is used according to the present invention is expected to be used for a safe and simple means for enhancing an immune response in a peptide vaccine or a DNA vaccine aimed at prophylaxis and treatment of Alzheimer disease.

---

The invention claimed is:

1. A peptide consisting of peptide (a) and peptide (b), wherein:

peptide (a) is selected from the group consisting of a peptide of the amino acid residues No. 1 to No. 10 from the N-terminal of SEQ ID NO:1, a peptide of the amino acid residues No. 2 to No. 10 from the N-terminal of SEQ ID NO:1, a peptide of the amino acid residues No. 3 to No. 10 from the N-terminal of SEQ ID NO:1, a peptide of the amino acid residues No. 1 to No. 9 from the N-terminal of SEQ ID NO:1, a peptide of the amino acid residues No. 2 to No. 9 from the N-terminal of SEQ ID NO:1, and a peptide of the amino acid residues No. 1 to No. 18 from the N-terminal of SEQ ID NO:1, and peptide (b) is selected from the group consisting of a peptide of the amino acid residues No. 28 to No. 36 from the N-terminal of SEQ ID NO:1, a peptide of the amino acid residues No. 28 to No. 37 from the N-terminal of SEQ ID NO:1, a peptide of the amino acid residues No. 28 to No. 38 from the N-terminal of SEQ ID NO:1, a peptide of the amino acid residues No. 28 to No. 39 from the N-terminal of SEQ ID NO:1, a peptide of the amino acid residues No. 28 to No. 40 from the N-terminal of SEQ ID NO:1, a peptide of the amino acid residues No. 28 to No. 41 from the N-terminal of SEQ ID NO:1, and a peptide of the amino acid residues No. 28 to No. 42 from the N-terminal of SEQ ID NO:1, wherein the C-terminal of peptide (a) is bound to the N-terminal of peptide (b), and wherein cysteine or a cysteine analog is bound to the C-terminal of a resulting combination of peptide (a) and peptide (b).

2. The peptide of claim 1, wherein a cysteine analog is bound to the C-terminal of the resulting combination of peptide (a) and peptide (b), and the cysteine analog is homocysteine.

3. The peptide of claim 1, wherein the peptide
has a sequence of any one of SEQ ID NO:2 to SEQ ID NO:13.

4. The peptide of claim 1, wherein the peptide has a sequence of SEQ ID NO:2.

5. The peptide of claim 1, wherein the peptide has a sequence of SEQ ID NO:3.

6. The peptide of claim 1, wherein the peptide has a sequence of SEQ ID NO:4.

7. The peptide of claim 1, wherein the peptide has a sequence of SEQ ID NO:5.

8. The peptide of claim 1, wherein the peptide has a sequence of SEQ ID NO:6.

9. The peptide of claim 1, wherein the peptide has a sequence of SEQ ID NO:7.

10. The peptide of claim 1, wherein the peptide has a sequence of SEQ ID NO:8.

11. The peptide of claim 1, wherein the peptide has a sequence of SEQ ID NO:9.

12. The peptide of claim 1, wherein the peptide has a sequence of SEQ ID NO:10.

13. The peptide of claim 1, wherein the peptide has a sequence of SEQ ID NO:11.

14. The peptide of claim 1, wherein the peptide has a sequence of SEQ ID NO:12.

15. The peptide of claim 1, wherein the peptide has a sequence of SEQ ID NO:13.

16. A medicament, comprising, as an active ingredient, the peptide of claim 1,
wherein the medicament is suitable for treatment of Alzheimer disease.

17. A method for inducing an immune response to amyloidβ, comprising administering to a subject in need thereof, an effective amount of the peptide of claim 1.

18. A method for making a medicine, comprising combining the peptide of claim 1 with a pharmaceutically acceptable carrier.

* * * * *